United States Patent
De Ridder

(10) Patent No.: US 10,780,277 B2
(45) Date of Patent: *Sep. 22, 2020

(54) METHODS OF NEUROMODULATION USING INFRASLOW STIMULATION

(71) Applicant: Dirk De Ridder, Dunedin (NZ)

(72) Inventor: Dirk De Ridder, Dunedin (NZ)

( * ) Notice: Subject to any disclaimer, the term of this patent is extended or adjusted under 35 U.S.C. 154(b) by 275 days.

This patent is subject to a terminal disclaimer.

(21) Appl. No.: 15/585,984

(22) Filed: May 3, 2017

(65) Prior Publication Data

US 2017/0333715 A1    Nov. 23, 2017

Related U.S. Application Data

(63) Continuation-in-part of application No. 15/078,819, filed on Mar. 23, 2016, now Pat. No. 10,118,038, and a continuation-in-part of application No. 14/851,540, filed on Sep. 11, 2015, now Pat. No. 10,076,668.

(60) Provisional application No. 62/331,314, filed on May 3, 2016, provisional application No. 62/137,587, filed on Mar. 24, 2015, provisional application No. 62/049,086, filed on Sep. 11, 2014.

(51) Int. Cl.
*A61N 1/00* (2006.01)
*A61N 1/36* (2006.01)
*A61N 1/05* (2006.01)

(52) U.S. Cl.
CPC .......... *A61N 1/36082* (2013.01); *A61N 1/05* (2013.01); *A61N 1/36139* (2013.01); *A61N 1/36171* (2013.01); *A61N 1/36192* (2013.01); *A61N 1/36196* (2013.01); *A61N 1/00* (2013.01); *A61N 1/0529* (2013.01); *A61N 1/0551* (2013.01); *A61N 1/36067* (2013.01); *A61N 1/36178* (2013.01)

(58) Field of Classification Search
CPC .. A61N 1/0531; A61N 1/0536; A61N 1/0541; A61N 1/056; A61N 1/059; A61N 1/36171; A61N 1/36178; A61N 1/36164; A61N 1/36082

See application file for complete search history.

(56) References Cited

U.S. PATENT DOCUMENTS

| | | | | |
|---|---|---|---|---|
| 5,983,141 A | * | 11/1999 | Sluijter | A61N 1/403 607/100 |
| 2006/0095088 A1 | * | 5/2006 | De Ridder | A61N 1/0529 607/48 |
| 2009/0093858 A1 | * | 4/2009 | DiUbaldi | A61N 1/0514 607/17 |

* cited by examiner

*Primary Examiner* — Mallika D Fairchild

(57) ABSTRACT

Methods are provided to treat a neurological disorder in a patient by adjusting connectivity between network nodes in a brain of patient using electrical stimulation. Electrical stimulation including a carrier wave component is employed to adjust connectivity using infraslow frequencies of less than 1 Hz.

8 Claims, 15 Drawing Sheets

METHODS OF NEUROMODULATION USING INFRASLOW STIMULATION

RELATED APPLICATION

The present application is a continuation-in-part of U.S. patent application Ser. No. 14/851,540, filed Sep. 11, 2015 which claims priority to U.S. Patent Application Ser. No. 62/049,086 filed Sep. 11, 2014. The present application is also a continuation-in-part of U.S. patent application Ser. No. 15/078,819, filed Mar. 23, 2016 which claims priority to U.S. Patent Provisional Application Ser. No. 62/137,587 filed Mar. 24, 2015. This application also claims priority to U.S. Patent Provisional Application Ser. No. 62/331,314 filed May 3, 2016. All of these applications are incorporated herein by reference in their entirety.

BACKGROUND

NS systems are devices that generate electrical pulses and deliver the pulses to nervous tissue to treat a variety of disorders. For example, spinal cord stimulation has been used to treat chronic and intractable pain. Another example is deep brain stimulation, which has been used to treat movement disorders such as Parkinson's disease and affective disorders such as depression. SCS therapy, delivered via epidurally implanted electrodes, is a widely used treatment for chronic intractable neuropathic pain of different origins. Traditional tonic therapy evokes paresthesia covering painful areas of a patient. During SCS therapy calibration, the paresthesia is identified and localized to the painful areas by the patient in connection with determining correct electrode placement.

Recently, new stimulation configurations such as burst stimulation and high frequency stimulation, have been developed, in which closely spaced high frequency pulses are delivered. In general, conventional neurostimulation systems seek to manage pain and other pathologic or physiologic disorders through stimulation of select nerve fibers that carry pain related signals. However, nerve fibers and brain tissue carry other types of signals, not simply pain related signals.

Although some neurological disorders have been treated through known neurostimulation methods, many other neurological disorders exhibit physiological complexity, functional complexity, or other complexity and have not been adequately treated through known neurostimulation methods.

SUMMARY

In accordance with embodiments disclosed herein, optimal targets within the nervous system are selected for neuromodulation. The optimal targets are selected according to network connectivity within the nervous system of a patient according to selected embodiments. For example, the brain of a patient may be modeled as a complex adaptive system of one or more neural networks. The brain may be viewed as exhibiting small world topology characteristics. That is, the brain functions as a modular scale free hierarchical network (e.g., fractal in organization). Also, the brain functions in the presence of noise (equivalently variability in neural activity). In a noisy, hierarchical organization, the brain functions as a complex adaptive network of interconnected modules. By selecting one or more nodes within one or more networks within the brain for stimulation, a neurological disorder may be treated by strengthening or weakening the network connectivity to treat an identified neurological disorder.

Certain connectivity between neural populations in the brain may be defined by structural connectivity. The structural connectivity may be determined using diffusion tensor imaging (DTI), diffusion spectrum imaging (DSI) or diffusion kurtosis imaging (DKI) as examples. Connectivity may also be the result of functional connectivity in a network. The functional connectivity may be determined by correlation in neural activity in one or more respective brain areas or brain networks. Also, connectivity may be related to effective connectivity, which can be considered directional functional connectivity, through the result of information transfer between neural nodes and networks.

Improper connectivity from a neurological disorder is addressed according to embodiments disclosed herein. In some embodiments, insufficient or decreased functional and/or effective connectivity related to a neurological disorder is strengthened by simultaneous or otherwise synchronized stimulation in two or more nodes of one or more neural networks relevant to the neurological disorder or by burst stimulation in a single hub of a network In some embodiments, excessive functional and/or effective connectivity related to a neurological disorder is weakened by asynchronous or randomized stimulation in one or more hubs of a neural network relevant to the respective neurological disorder.

In a network connectivity framework, the centrality of a node refers to how many of the shortest paths between all other node pairs in a network pass through the respective node. As discussed herein, a hub refers to a network node in a neurological network which exhibits a high degree of centrality. Neurological hubs connect to may other brain areas. "Rich club" neurological sites refer to neurological sites that are hubs and are connected to many other hubs. Rich club sites integrate neurological activity from different networks and different neurological modules.

According to some embodiments, sites for neuromodulation are selected according to identified hubs (for example feeder hubs or hubs of the rich club or core) By selecting hub and rich club sites, improper connectivity (associated with a given neurological disorder) can be more effectively strengthened or weakened depending upon the specific neurological disorder.

In some embodiments, network stimulation may include stimulation of one or more peripheral nerves, autonomic nerves (vagal, sympathetic nerves), sensory nerves, auditory nerves, and/or the spinal cord, in addition to stimulation of sites in the brain.

Multiple types of stimulation patterns may be employed for network stimulation according to respective embodiments including tonic, burst, and noise stimulation patterns as examples.

In some embodiments, nested stimulation may be provided to one or more nodes within one or more neural networks in association with adjusting connectivity within or between one or more networks. Details regarding nested stimulation may also be found in U.S. patent application Ser. No. 14/851,540, entitled "SYSTEM AND METHOD FOR NESTED NEUROSTIMULATION," which is incorporated herein by reference.

DETAILED DESCRIPTION

Figure 1A:
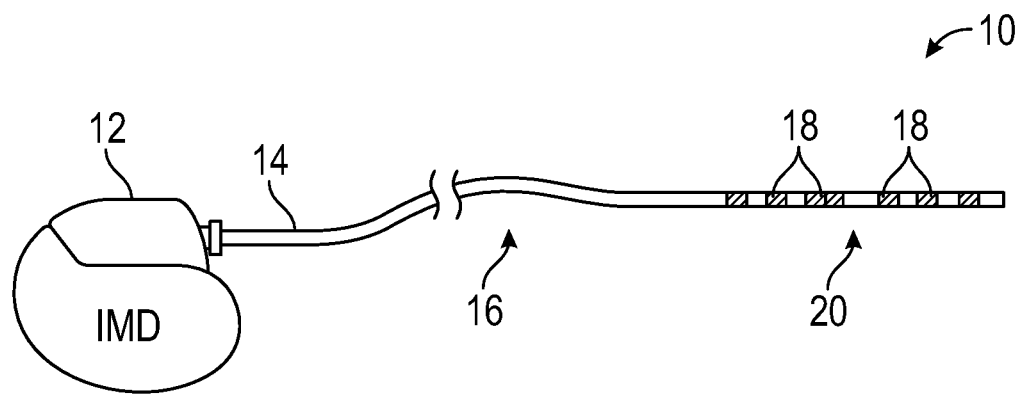
FIG. 1A illustrates an example neurological stimulation (NS) system for electrically stimulating a predetermined site area to treat one or more neurological disorders or conditions in accordance with embodiments herein.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

I. Definitions

Unless defined otherwise, technical and scientific terms used herein have the same meaning as commonly understood by one of ordinary skill in the art to which this invention belongs. For purposes of the description, the following terms are defined below. Further, additional terms are used herein that shall have definitions consistent with the definitions set forth in U.S. Pat. No. 8,401,655, which is expressly incorporated herein by reference in its entirety.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

As used herein, the term "burst firing" or "burst mode" refers to an action potential that is a burst of high frequency spikes/pulses (e.g. 400-1000 Hz) (Beunrrier et al., 1999). Burst firing acts in a non-linear fashion with a summation effect of each spike/pulse. One skilled in the art is also aware that burst firing can also be referred to as phasic firing, rhythmic firing (Lee 2001), pulse train firing, oscillatory firing and spike train firing, all of these terms used herein are interchangeable.

As used herein, the term "tonic firing" or "tonic mode" refers to an action potential that occurs in a linear fashion.

As used herein, the term "burst" refers to a period in a spike train that has a much higher discharge rate than surrounding periods in the spike train (N. Urbain et al., 2002). Thus, burst can refer to a plurality of groups of spike pulses. A burst is a train of action potentials that, possibly, occurs during a 'plateau' or 'active phase', followed by a period of relative quiescence called the 'silent phase' (Nunemaker, Cellscience Reviews Vol 2 No. 1, 2005.) Thus, a burst comprises spikes having an inter-spike interval in which the spikes are separated by 0.5 milliseconds to about 100 milliseconds. Those of skill in the art realize that the inter-spike interval can be longer or shorter. Yet further, those of skill in the art also realize that the spike rate within the burst does not necessarily occur at a fixed rate; this rate can be variable.

The terms "pulse" and "spike" are used interchangeably to refer to an action potential. Yet further, a "burst spike" refers to a spike that is preceded or followed by another spike within a short time interval (Matveev, 2000), in other words, there is an inter-spike interval, in which this interval is generally about 100 ms but can be shorter or longer, for example 0.5 milliseconds.

In accordance with embodiments disclosed herein, the brain of a patient is modeled as a complex adaptive system of one or more neural networks. The brain may be viewed as exhibiting small world topology characteristics. That is, the brain functions as a modular scale free hierarchical network (e.g., fractal in organization). Also, the brain functions in the presence of noise (equivalently variability in neural activity)—see, for example, U.S. Pat. No. 8,682,441 by De Ridder, which is incorporated herein by reference. In a noisy, hierarchical organization, the brain functions as a complex adaptive network of interconnected modules. By selecting multiple nodes within one or more networks within the brain for stimulation, a neurological disorder may be treated by strengthening or weakening the network connectivity within a single network or between multiple networks. The nodes for neuromodulation are selected according to network hubs and/or rich club sites according to some embodiments.

Certain connectivity between neural populations in the brain may be defined by structural connectivity. The structural connectivity may be determined using diffusion tensor imaging (DTI) or diffusion spectrum imaging (DSI) as examples.

Connectivity may also be the result of functional connectivity in a network. The functional connectivity may be determined by correlation in activity in one or more respective networks using multiple electrodes to detect neural activity in relevant brain locations. Any number of suitable mechanisms may be employed to measure neuronal activity for suitable processing.

For example, EEG (or electroencephalogram) is a recording of brainwave activity. QEEG (Quantitative EEG), popularly known as brain mapping, refers to a comprehensive analysis of brainwave frequency bandwidths that make up the raw EEG. QEEG is recorded the same way as EEG, but the data acquired in the recording are used to create topographic color-coded maps that show electrical activity of the cerebral cortex.

In an QEEG analysis, the electrical activity of the brain is measured by placing a number of electrodes or sensors about the head of a patient and the sensors are connected to a recording device. Electrical activity is recorded using the sensors for typically ten to thirty minutes.

The data representing the recorded electrical activity is suitably processed. The processing provides complex analysis of brainwave characteristics such as symmetry, phase, coherence, amplitude, power and dominant frequency. Such processing enables the correlation, coherence, and relevant activity metrics indicative of functional connection between brain locations to be identified.

The analysis enables activity falling above or below a statistical norm to be identified for locations within the brain. Also, the activity may identify activity above or below the norm for relevant brainwave frequency bands (delta, theta, alpha, beta, and gamma bands as examples). The activity variance from the norm can be expressed relative to a calculated standard deviation of activity data.

Further, the QEEG analysis further enables functional connectivity to be identified by coherence analysis of activity between different neural sites. The functional connectivity can be likewise expressed in terms of above or below the norm relative to a standard deviation calculation.

Additional and/or alternative processing of recordings of electrical activity in the brain of a patient may be employed to assist identification of variations in functional connectivity related to a neurological disorder according to some embodiments. For example, QEEG combined with LORETA (Low Resolution Electromagnetic Tomography) enables examining of deep structures of the brain slice by slice, as well as viewing 3-dimensional models of the brain and may provide a suitable analysis to identify functional connectivity resulting from a neurological disorder to be treated according to representative embodiments.

Also, the BrainWave software application (available from the Department of Clinical Neurophysiology, VU University Medical Center, Amsterdam, The Netherlands) is an application for the analysis of multivariate neurophysiological data sets (such as EEG data sets). The BrainWave application provides several measures of functional connectivity (coherence, phase coherence, imaginary coherence, PLI and synchronization likelihood) among other relevant neural activity metrics. The functional connectivity mapping of the BrainWave application may be employed to assist identification of variations in functional connectivity related to a neurological disorder in a patient according to some embodiments.

In some embodiments, a network representation of neural activity is created using graph and network concepts. The graph representation may be patterned according to a mathematical representation of a neural network composed of interconnected elements or sites. The representation may involve construction and processing according to Graph Theory (mathematical study of graphs/networks). From the representation, the network topology of the neural activity may be analyzed according to mathematical analysis of shapes and spaces, concerned with the invariant properties of space that are preserved under continuous deformations (bending, stretching). Also, topological distance does not necessarily imply close physical distances. Thus, physical distances between nodes, transmission rates, and/or signal types may differ in two networks and yet their topologies may be identical.

Hubs are nodes with high degree (or high centrality). The degree of a node is the number of connections that link it to the rest of the network. Degrees of all the network's nodes form a degree distribution. Assortativity is the correlation between the degrees of connected nodes. Positive assortativity indicates that high-degree nodes tend to connect to each other (rich club). Clustering coefficient quantifies the number of connections that exist between the nearest neighbors of a node as a proportion of the maximum number of possible connections. Path length is the minimum number of edges that must be traversed to go from one node to another. Each module contains several densely interconnected nodes, and there are relatively few connections between nodes in different modules. Connection density is the actual number of edges in the graph as a proportion of the total number of possible edges and is the simplest estimator of the physical cost. Connection density is an indirect measure of global efficiency. Centrality of a node measures how many of the shortest paths between all other node pairs in the network pass through it.

Most brain disorders are hub disorders. For example, lesions in neural hubs are linked to amyotrophic lateral sclerosis, dystonia, developmental dyslexia, anorexia nervosa, obsessive-compulsive disorder, Parkinson's disease, hereditary ataxia, dementia in Parkinson's, chronic pain, panic disorder, attention deficit hyperactivity disorder, bipolar affective disorder, multiple sclerosis, frontotemporal dementia, obstructive sleep apnea, Autism, schizophrenia, Alzheimer's disease, Asperger syndrome, Huntington's disease, depressive disorder, right temporal lobe epilepsy, post traumatic stress disorder, progressive supranuclear palsy, left temporal lobe epilepsy, and juvenile myodonic epilepsy. Accordingly, representative embodiments employ neurostimulation of one or more hubs (possibly rich club sites or feeder hubs) to treat any of the neurological disorders discussed herein.

One or more hubs and/or rich club sites associated with a respective neurological disorder in a patient may be identified from the representation of neural activity generated by the measurement and processing operations discussed herein. The activity and cross-coupling between nodes, hubs, and/or rich club sites may be identified and compared to activity and coupling exhibited by healthy controls. Relevant deviations from the healthy controls are used to identify neural hubs and/or rich club sites for neuromodulation to treat the respective neurological disorder.

Improper neural connectivity (associated with neural hubs and rich club or core sites) as detected using the operations discussed herein is addressed using neuromodulation of identified sites. As previously discussed, various EEG, MEG or functional MRI measurements and processing may be employed to analyze coupling associated with respective hubs. Coupling between respective sites may be identified, for example, in reference to envelope correlation of neural activity at the various neural sites. The improper coupling can be treated by recoupling and uncoupling as appropriate for a given neurological disorder. In some embodiments, insufficient functional and/or effective connectivity related to a neurological disorder is strengthened by simultaneous or otherwise synchronized stimulation in relevant sites. In some embodiments, excessive functional and/or effective connectivity related to a neurological disorder is weakened by asynchronous or randomized or noise stimulation in relevant sites. The treatment methodology may also monitor the effectiveness of the therapy by determining whether connectivity is modified after stimulation using suitable activity measurement techniques and processing.

In some embodiments, functional connectivity may be strengthened by applying burst stimulation using a single electrode or electrode combination to stimulate relevant hub neurons. Burst stimulation of a hub site will trigger synchronous firing across the neural network containing the respective hub site. Also, burst stimulation may be applied simultaneously to two or more separate sets of electrodes in two or more hub or non-hub areas. The synchronization of burst stimulation in this manner will cause the neural connection between the two sites to be rewired and strengthened. Hub stimulation using this methodology may be use to treat traumatic brain injury and postconcussion syndrome and to prevent dementia pugilistica as examples. For example, suitable burst stimulation may be applied to a suitable thalamus site to strengthen functional connectivity in such patients.

In some embodiments, functional connectivity may be reduced by applying noise stimulation using a single electrode or electrode combination to stimulate relevant hub neurons functionally connected to a neural network associated with a relevant neurological disorder. For example, functional connectivity may arise in addiction disorders. Neural activity in the dACC becomes functionally coupled to activity in the PCC. Activity in these areas are normally anticorrelated. The functional connectivity caused by the addiction disorder may be treated by noise stimulation in the dACC or PCC. Alternatively, noise stimulation in the dACC and burst stimulation in the PCC may be applied to treat addiction in some embodiments. These techniques for dACC and PCC stimulation to adjust functional connectivity may also be employed to treat patients with depression and/or anxiety disorders.

In some embodiments, hub stimulation is applied to a patient specifically to generate anticorrelated activity in respective areas of the brain. In some neurological disorders such as loss of consciousness, addiction, OCD, chronic pain, tinnitus, etc., there is less or no more anticorrelated activity between two or more networks. Most commonly, this reduction or lack of anticorrelated activity is exhibited between the default mode network and the salience network, but it also occurs between other areas such as the dorsal ACC and pregenual ACC. By using burst stimulation and noise stimulation simultaneously in the respective networks that need to become anticorrelated, the underlying neurological disorder is treated according to some embodiments. In these embodiments, one or more hubs in the default mode network are selected for stimulation such as posterior cingulate cortex (PCC) and precuneus. Also, one or more hubs in the salience network are selected for stimulation such as the anterior cingulate cortex (ACC) and insula. Using electrodes implanted at these sites, burst stimulation is applied for 10 seconds (for example) to the PCC and simultaneous noise stimulation applied to the ACC followed by 10 seconds of bursting in ACC and simultaneous noise stimulation in the PCC. This repetition of noise and burst in the respective areas is then repeated over an appropriate amount of time. This stimulation pattern induces or promotes anticorrelated activity in the two networks (default mode network and salience network). This stimulation methodology is believed to benefit patients with addiction, OCD, pain, tinnitus, etc. Also, this stimulation methodology may be employed to assist patients in a coma, a vegetative state or a minimal conscious state to regain consciousness.

In some embodiments, functional connectivity may be modified by applying suitable stimulation to the nucleus accumbens and other relevant sites. For example, respective electrodes may be employed to stimulate nucleus accumbens and pregenual ACC and/or vmPFC sites to adjust functional connectivity to treat relevant neurological disorders including OCD. Stimulation of pgACC and accumbens sites to adjust functional connectivity may be employed to treat patients with chronic pain.

Figure 10:
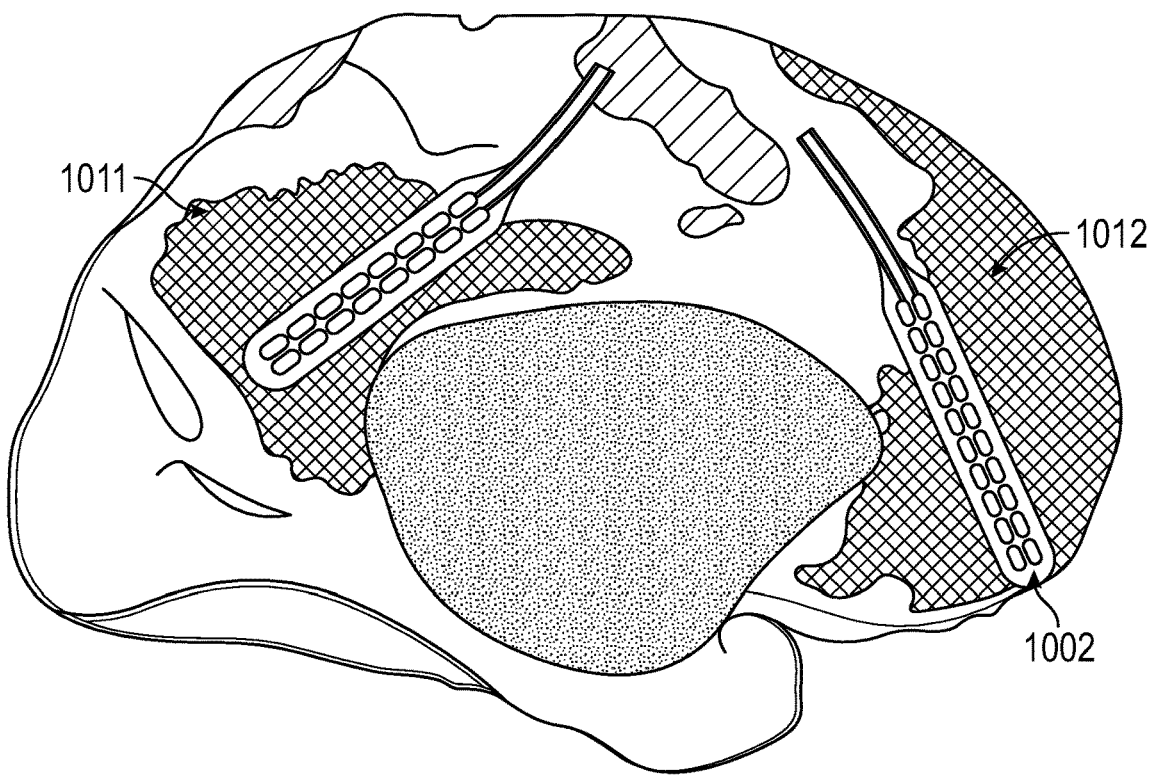
FIG. 10 illustrates leads implanted for stimulation of neural networks to adjust connectivity according to embodiments herein.

FIG. 10 depicts a patient with implanted cortical leads 1001 and 1002. Lead 1001 is disposed over region 1011 and lead 1002 is disposed over region 1012. One or both of regions 1011 and 1012 may be a hub and/or a rich club neural site within a neurological network. The various electrodes of leads 1001 and 1002 may be employed to deliver electrical pulses to appropriate sites within regions 1011 and 1012. For a neurological disorder that exhibits weakened functional connectivity between a first site within region 1011 and a second site within region 1002, repetitive synchronous stimulation of the first site and the second site will increase the functional connectivity between these sites. For example, the synchronous stimulation may involve repetitively providing a stimulation pulse to the first site and then providing a stimulation pulse to the second site with a defined delay relative to the first site. The repetition of providing synchronized stimulation pulses may occur at suitable frequencies from 0.01 to 600 Hz, but most commonly between 0.1 Hz and 40 Hz. Tonic, burst stimulation, nested stimulation, and the suitable stimulation patterns may be applied with suitable synchronization. For a neurological disorder that exhibits excessive functional connectivity between a first site within region 1011 and a second site within region 1012, random or asynchronous stimulation patterns may be applied via suitable electrodes of leads 1001 and 1002. Although two sites are described herein, network stimulation may include stimulation of three or more network nodes according to embodiments described herein.

Brain function depends on activity in multiple parallel networks and some subsets of parallel networks function in an anti-correlated manner. That is, one network is active and simultaneously the other network is inactive when the brain is functioning properly. When disease or injury occurs, the anti-correlation between activity in certain networks may be reduced or disappear. Anticorrelation can occur at different frequencies, between 0.01 and 600 Hz, but most commonly between 0.1 and 40 Hz.

In some embodiments, hub stimulation is augmented by stimulation of the reward system. Suitable locations within the reward system for stimulation may include one or more locations selected from the list consisting of: the nucleus accumbens (NAc), caudate nucleus, the laterodorsal tegmentum, ventral tegmental area (VTA), the ventral *pallidum*, the subthalamic nucleus (STN), medial dorsal nucleus of the thalamus, and the posterior cingulate cortex (PCC), as well as the ventral tegmental area, pregenual, rostral or dorsal anterior cingulate cortex, as well as the anterior and/or posterior insula or the fiber bundles connecting either of these areas. Additional details regarding stimulation of the reward network of a patient may be found in U.S. Provisional Patent Application Ser. No. 62/007,058, entitled "METHOD OF TREATING A NEUROLOGICAL DISORDER IN A PATIENT (RECONDITIONING)" filed Jun. 3, 2014, which is incorporated herein by reference.

Stimulation of a suitable site in the reward network of a patient in conjunction with strengthening or weakening network connectivity between other network sites facilitates a permanent change in the connectivity between those network sites. Specifically, a conditioning effect occurs to retain the desired modification in connectivity. In some embodiments, a burst stimulation pattern is applied to a nucleus accumbens site, a PCC site, or a caudate nucleus site to generate the conditioning effect.

Figure 11:
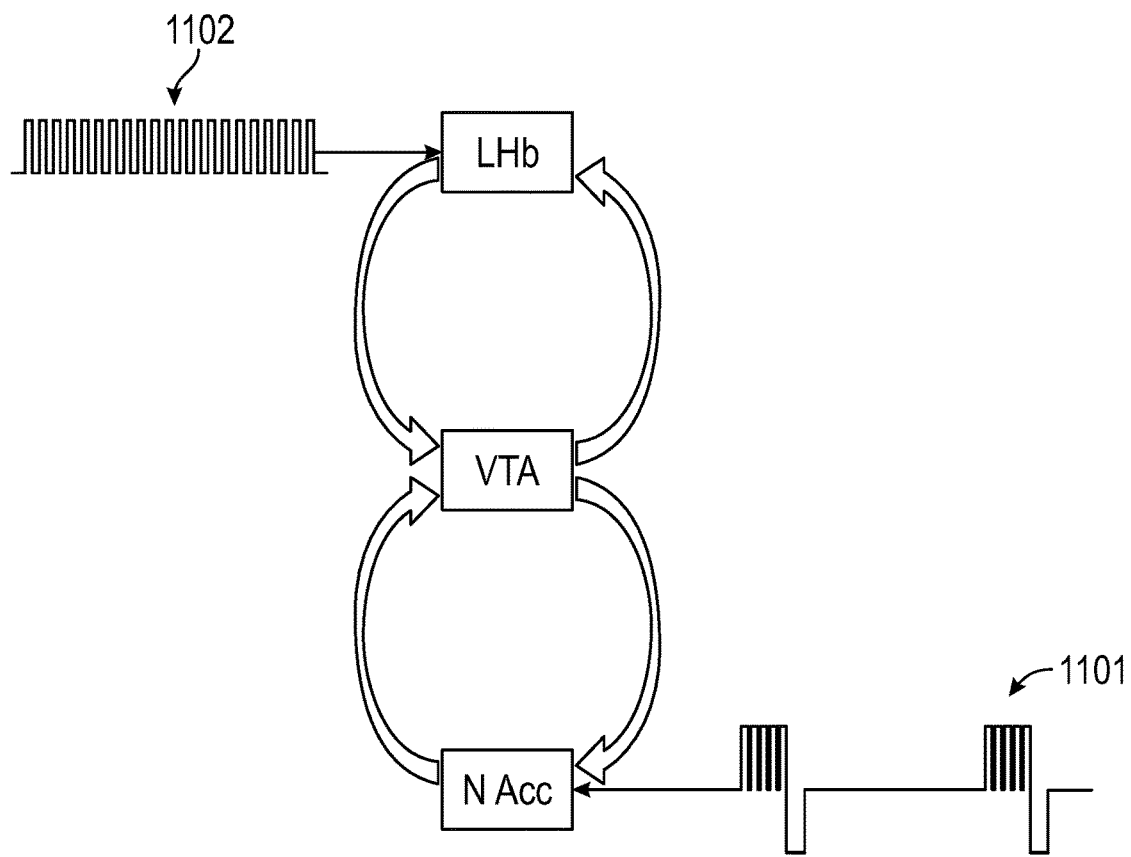
FIG. 11 illustrates stimulation of the reward network in conjunction with adjusting network connectivity according to embodiments herein.

FIG. 11 depicts stimulation of neuronal sites within the reward network of a patient according to some embodiments. In FIG. 11, burst stimulation 1101 is provided to the nucleus accumbens. This could include clustered high frequency stimulation, e.g. 5 to 100 individually charge balanced pulses delivered at 100-500 Hz. Optionally, high frequency stimulation 1102 (e.g., approximately 100 Hz or greater) is provided to lateral habenula the while burst stimulation 1101 is provided to the nucleus accumbens. Stimulation 1102 blocks activity of the lateral habenula, either by disrupting habenula activity or by driving habenula activity at specific frequencies from providing input to the VTA while input from the nucleus accumbens to the VTA occurs (as a result of burst stimulation 1101). The stimulation within structures of the reward network are provided to the patient immediately after or simultaneously with or immediately before stimulation is provided, as long as it is consistently associated, to adjust connectivity within one or more neural networks of the patient according to some embodiments.

In some embodiments, network stimulation may include stimulation of one or more peripheral nerves, autonomic nerves (vagal, sympathetic nerves), sensory nerves, auditory nerves, and/or the spinal cord, in addition to stimulation of sites in the brain.

In certain embodiments, network stimulation is used to treat neurological disorders involving stress, salience, and distress processes in a patient. In relevant neurological disorders, increased functional connectivity of the amygdala, dorsal anterior cingulate cortex (dACC), insula, and lateral cortex results in an extended state of hypervigilance. This promotes sustained salience and mnemonic processing. For example, tinnitus/pain remains constant. It has been observed that tinnitus is exhibited in 50% of post-traumatic stress disorder (PTSD), tortured patients. Randomized or otherwise asynchronous stimulation within multiple nodes within these networks may be employed to treat the neurological disorder.

Figure 12:
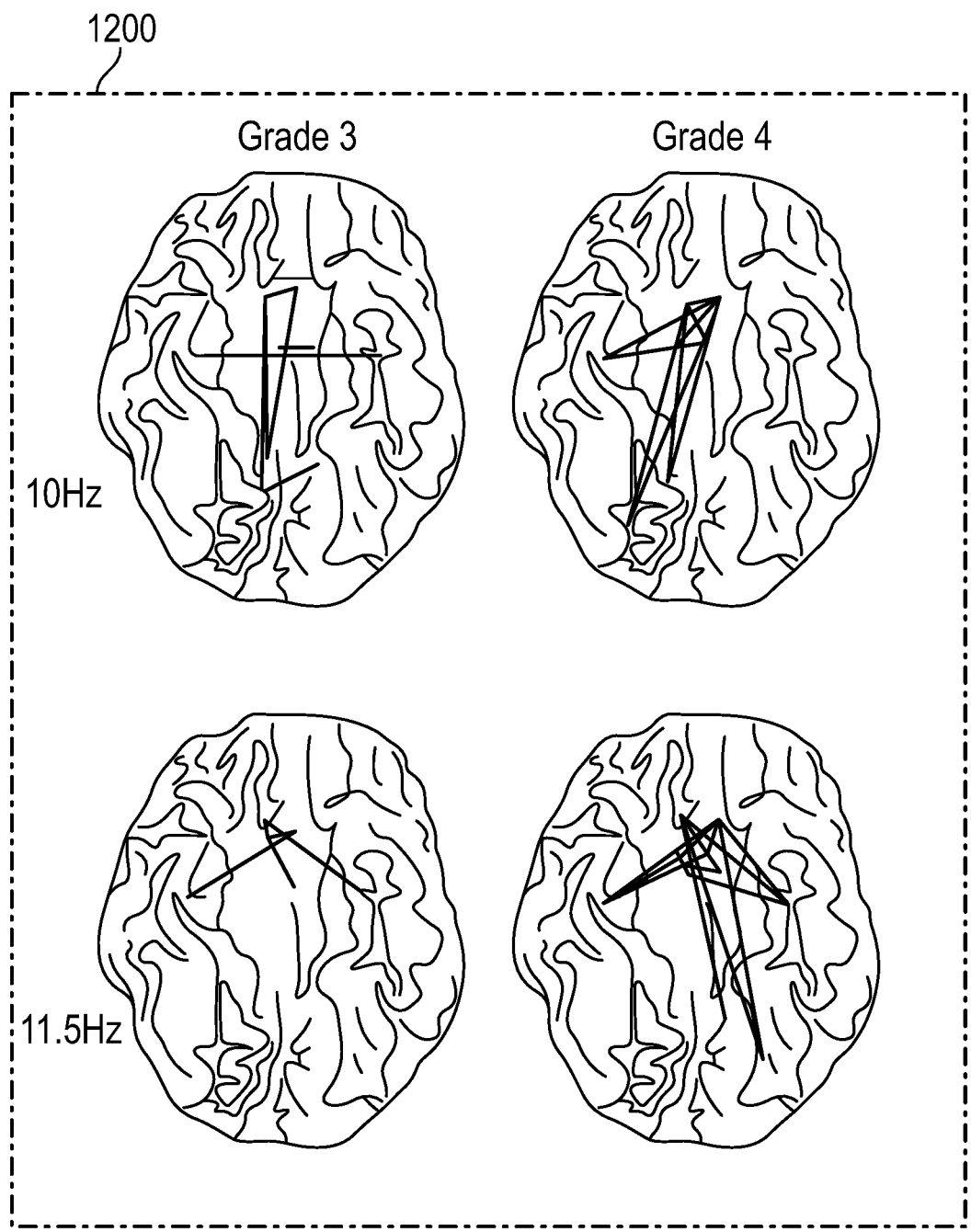
FIG. 12 illustrates leads implanted for stimulation of neural networks to adjust connectivity to treat tinnitus according to embodiments herein.

FIG. 12 depicts functional connectivity graphs 1200 related to tinnitus. Connectivity graphs 1200 may be created by analyzing neural activity of a patient to identify appropriate areas for neuromodulation according to some embodiments. In some embodiments, the treatment methodology involves identifying frequencies of neural activity associated with improper neural network connectivity. Connectivity graphs 1200 represent correlated neural activity at specific frequencies (10 Hz and 11.5 Hz). Also, connectivity graphs 1200 depict the connectivity for respective levels of tinnitus (severe/Grade 3 and very severe/Grade 4). As shown in FIG. 12, there is functional connectivity between the loudness network and the distress network. Specifically, there is increased functional connectivity between parahippocampal cortex (PCC) and subgenual anterior cingulate cortex (sgACC). Some representative embodiments treat tinnitus by stimulating respective sites in these two regions using randomized or asynchronous electrical stimulation.

Figure 13:
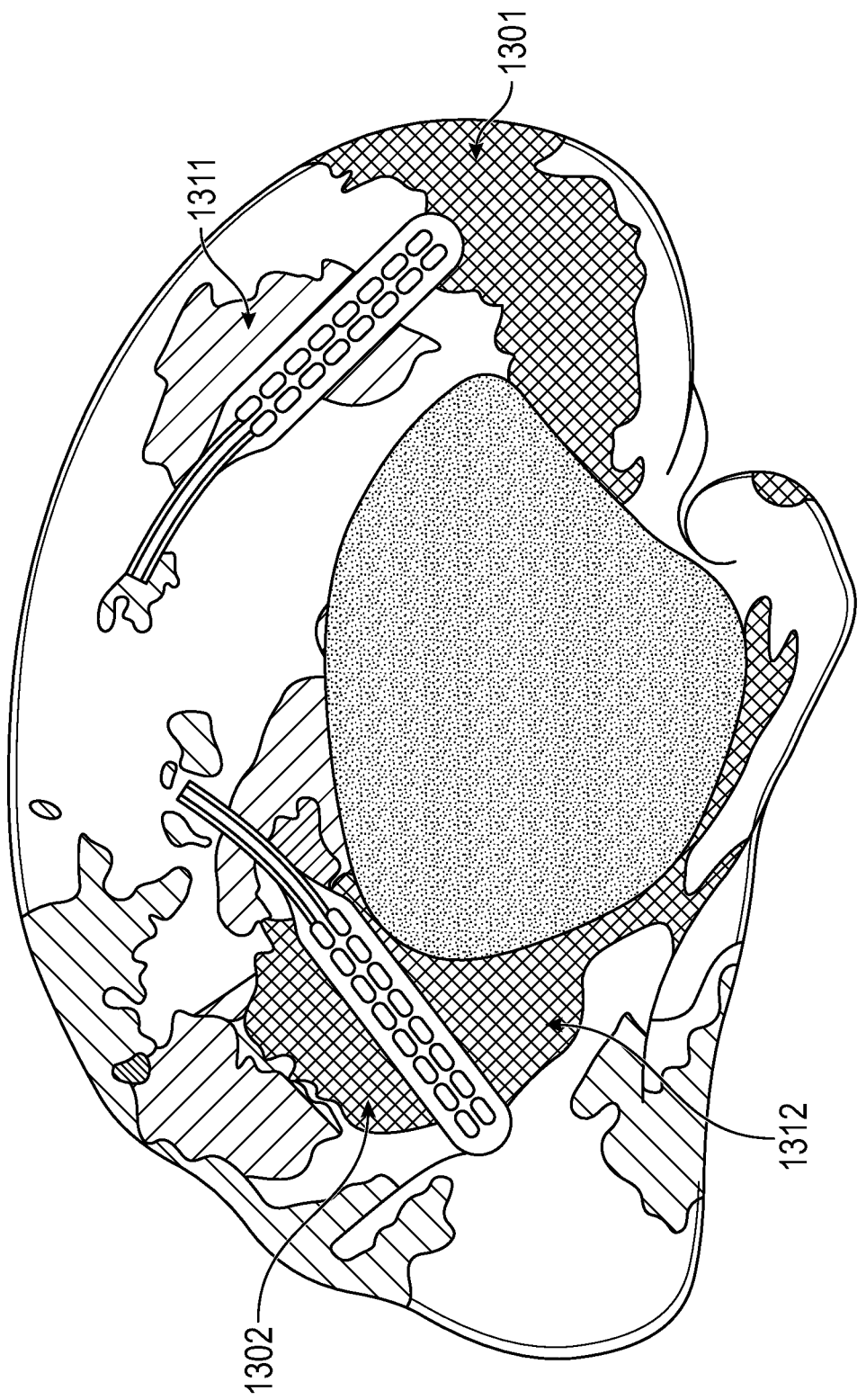
FIG. 13 depicts a stimulation lead (hippocampal-cortical memory system (HCMS)) over region 1311 and a stimulation lead over region 1312 (frontoparietal control system (FPCS)) to deliver neurostimulation according to some embodiments.

In accordance with representative embodiments, hub stimulation is employed to treat addiction-related neurological disorders. Repeated use of mood altering substances and other compounds may lead to unhealthy functional connectivity in neural networks in a patient. FIG. 13 depicts stimulation lead 1301 (hippocampal-cortical memory system (HCMS)) over region 1311 and stimulation lead 1302 over region 1312 (frontoparietal control system (FPCS)). In patients exhibiting neurological effects of addiction, regions 1311 and 1312 will often exhibit an unhealthy level of functional connectivity. In representative embodiments, one or more electrodes of stimulation lead 1301 and one or more electrodes of stimulation lead 1302 are employed to provide randomized or asynchronous electrical stimulation of regions 1301 and 1302. The randomized or asynchronous electrical stimulation of these regions is believed to reduce or eliminate neurological processes related to the addiction of the patient. Addiction is but an example, as all reward deficiency syndromes can potentially be treated with this embodiment. Reward deficiency syndromes include the brain disorders mentioned in the table (Blum, Molecular Neurobiology 2014)

according to respective embodiments stimulate neuronal sites according to different types of physiological neural oscillations or "brain waves" across the cortex. The different types of neural oscillation or brain wave activity can be decomposed into distinct frequency bands that are associated with particular physiologic and pathologic characteristics.

TABLE 1

| Reward deficiency syndrome behaviors (linked with DSM 5) | | | | | |
|---|---|---|---|---|---|
| Addictive behaviors | | Impulsive behaviors | | Obsessive compulsive | Personality |
| Substance related | Non substance related | Spectrum disorders | Disruptive impulsive | behaviors | disorders |
| Alcohol | Thrill seeking (novelty) | Attention-delicit hyperactivity | Anti-social | Body dysmorphic | Paranoid |
| Cannabis | Sexual sadism | Tourette and tic Syndrome | Conduct | Hoarding | Schizoid |
| Opioids | Sexual masochism | Autism | Intermittent explosive | Trichotillomania (hair pulling) | Borderline |
| Sedatives/hypnotics | Hypersexual | | Oppositional defiant | Excoriation (skin picking) | Schizotypal |
| Stimulants | Gambling | | Exhibitionistic | Non-suicidal self-injury | Histrionic |
| Tobacco | Internet gaming | | | | Narcissistic |
| Glucose | | | | | Avoidant |
| Food | | | | | Dependant |

In accordance with representative embodiments, cognitive disorders may result in decrease functional connectivity within neural networks and between neural networks. For example, among the several conditions labeled as dementia, the most common are Alzheimer's disease and mild cognitive impairment (MCI), which is a pre-clinical form of Alzheimer's disease. MCI is an intermediate state between normal aging and dementia and is characterized by acquired cognitive deficits, without significant decline in functional activities of daily living. Subjects with MCI and the initial phase of Alzheimer's disease originally present with a predominant deficit in memory function. In more advanced stages of Alzheimer's disease, impairment in addition cognitive domains culminates with a significant decline in quality of life and the inability to perform usual daily activities. In patient's exhibiting dementia and/or MCI, suitable analysis of neural activity may be performed to identify network node locations exhibiting improper connectivity. Synchronous stimulation of multiple sites may be employed to strengthen functional connectivity in such patients. For example, two, three, or more sites in the posterior cingulate cortex, frontal and parietal cortex, para-hippocampal area, hippocampus, and fornix or mammillary bodies may be repetitively stimulated in sequence to increase functional connectivity.

Stimulation of multiple nodes in one network or in multiple networks to adjust connectivity between the nodes may be employed to treat a number of neurological disorders. Neurological disorders involving excessive connectivity between distress neural network nodes and sensory network nodes (such as tinnitus and chronic pain) may be addresses using hub stimulation. Neurological disorders exhibiting diminished cognitive abilities may benefit from hub stimulation (such as dementia. MCI, TBI, trauma disorders). Various network locations may be selected for strengthening connectivity for such disorders (such as frontal cortex network sites, memory network sites). Also, addiction disorders, eating disorders, and related disorders may be also be treated using suitable hub stimulation techniques as described herein.

Figure 3:
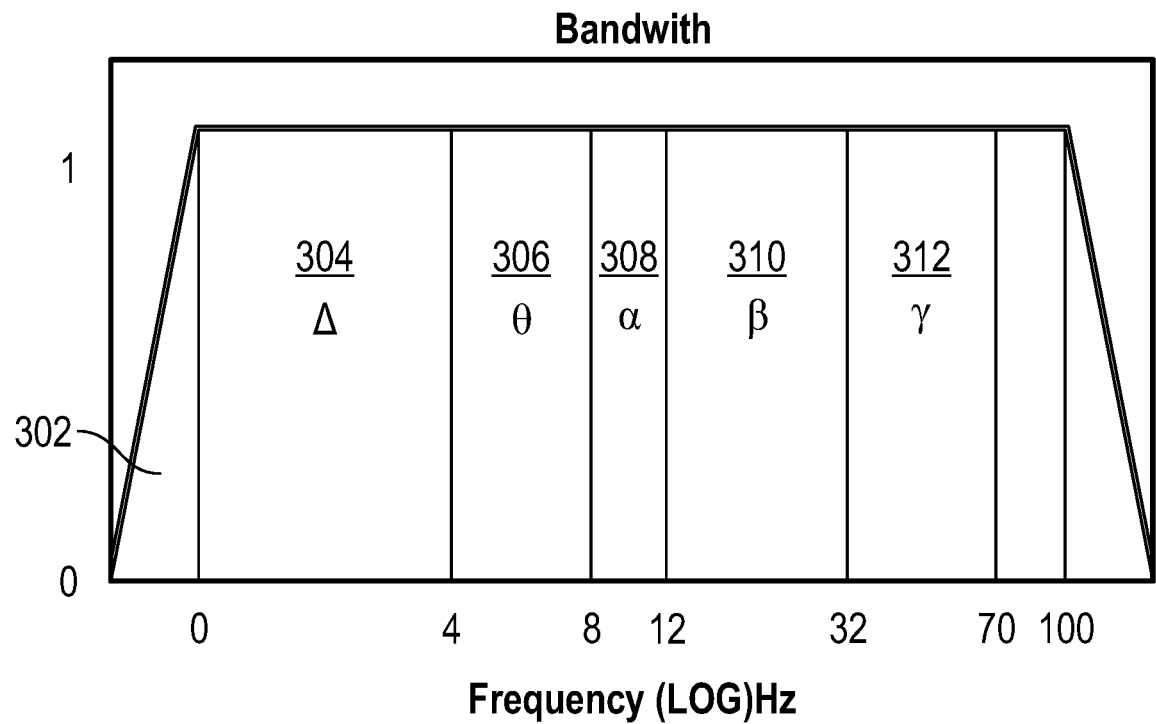
FIG. 3 illustrates an example of the various brainwave frequency bands in accordance with embodiments herein.
Figure 4A:
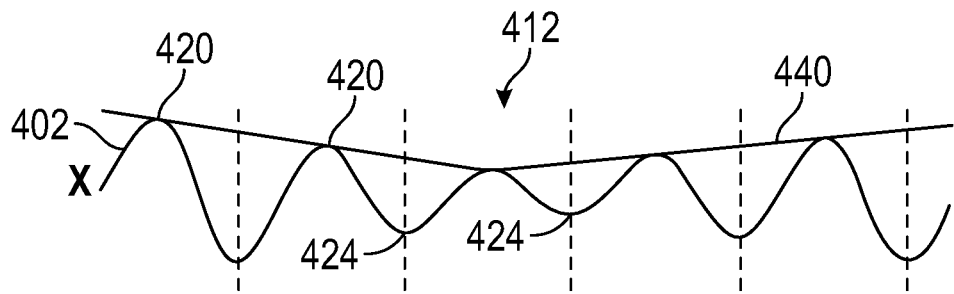
FIGS. 4A-4G illustrate examples of cross frequency coupling variations that may be used in accordance with embodiments herein.
Figure 4B:
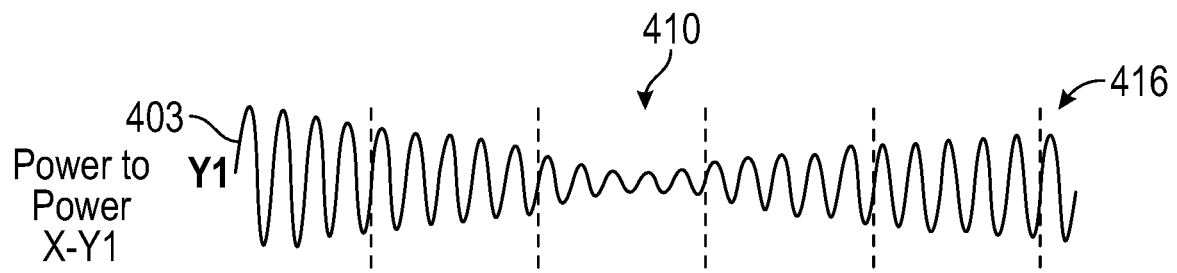
Figure 4C:
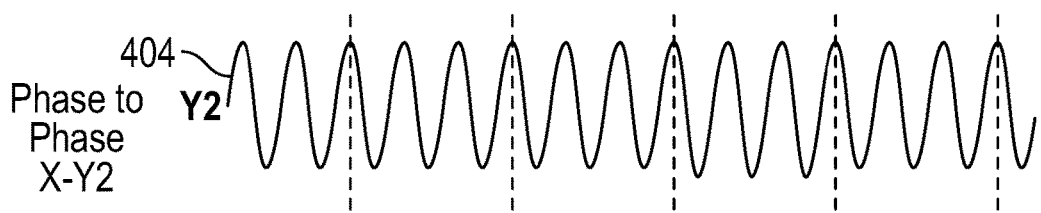
Figure 4D:
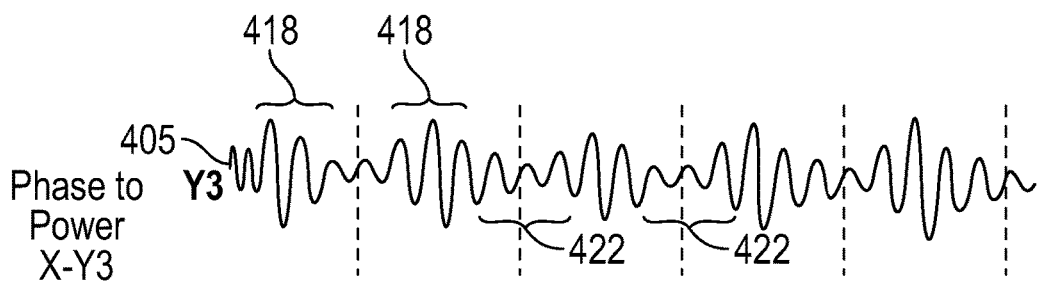
Figure 4E:
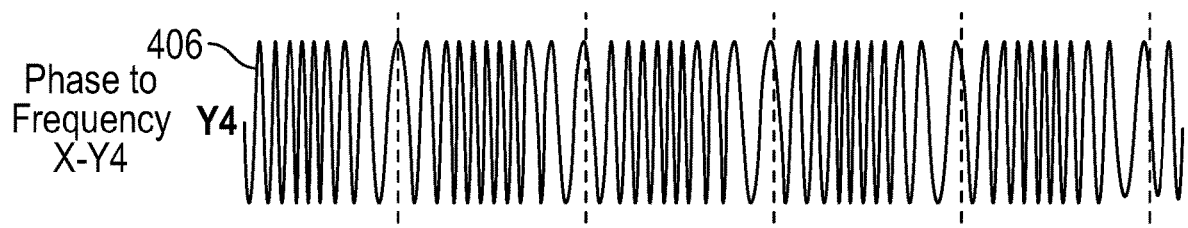
Figure 4F:
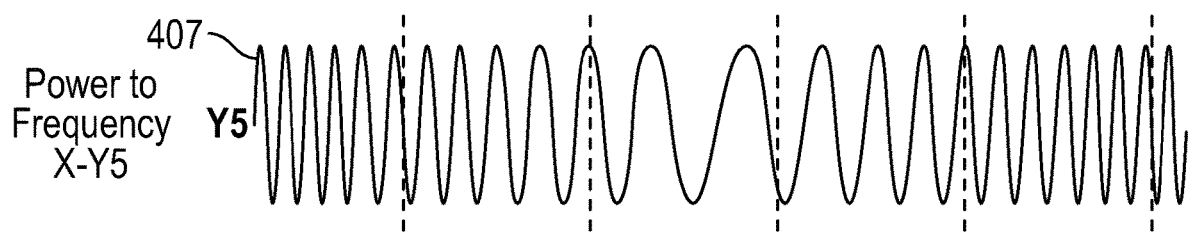
Figure 4G:
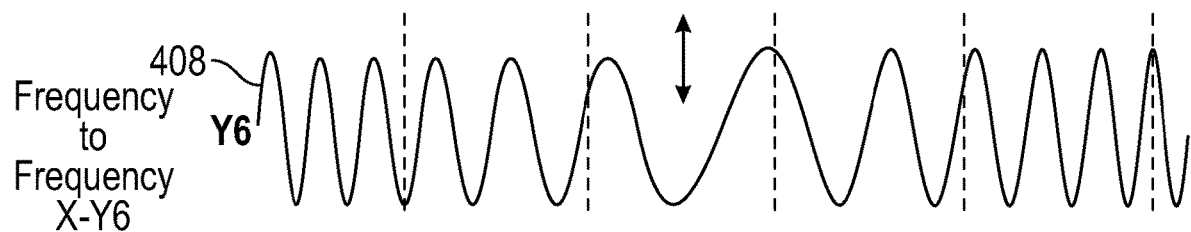

In some embodiments, nested stimulation may be also applied to one or more neural network sites to treat a neurological disorder of a patient when effecting functional connectivity between network nodes. Nested stimulation FIG. 3 illustrates an example of the various brainwave frequency bands which include infraslow waves 302 (less than 1 Hz, generally 0.001-1.0 Hz, and 0.01-0.1 Hz in some embodiments); delta waves 304 (1-4 Hz); theta waves 306 (4-8 Hz); alpha waves 308 (8-12 Hz), beta waves 310 (12-30 Hz), gamma waves 312 (greater than 30 Hz), and sigma waves (not shown) (greater than 500 Hz). Individual brainwave frequency bands and combinations of brainwave frequency bands are associated with various mental, physical and emotional characteristics. It should be recognized that the cutoff frequencies for the frequency bands for the various types of brain waves are approximations. Instead, the cutoff frequencies for each frequency band may be slightly higher or lower than the examples provided herein.

Neural oscillations from various combinations of the brainwave frequency bands have been shown to exhibit coupling with one another, wherein one or more characteristics of one type of brainwave effect (or are affected by) one or more characteristics of another type of brainwave. In general, the coupling phenomenon is referred to as cross frequency coupling, various aspects of which are described in the papers referenced herein. Combinations of frequency bands couple with one another to different degrees, while the coupling of various types of brainwaves may occur in connection with physiologic behavior or pathologic behavior. For example, theta and gamma frequency coupling has been identified at the hippocampalcortical in connection with physiologic behavior, but in thalamocortical activity this same theta-gamma coupling should be considered pathological, as normal activity consists of alpha-gamma coupling, except in sleep stages Delta—gamma and delta—beta frequency coupling have been identified in connection with physiological reward system activity as well as in autonomic nervous system activity. As another example, alpha—gamma frequency coupling has been identified at the pulvinar region in connection with physiological processes mediating attention.

FIGS. 4A-4G illustrate examples of cross frequency coupling variations that may be used in accordance with embodiments herein. There are different principles of cross-frequency interactions. FIGS. 4A-4G illustrate various example brain waves 402-408. As one example, a carrier wave 402 may correspond to a slow oscillatory signal in the theta band (e.g. 8 Hz). Although the frequency remains fairly constant, the power (as denoted by line 440) of the signal fluctuates over time. The gamma oscillations can interact in different ways with other signal oscillations.

The brain waves 403-408 illustrate examples of how the carrier and secondary waves 402 and 403 may be combined. For example, the wave 403 as illustrated, has been frequency coupled to the carrier wave 402 in a power to power matter such that the amplitude of the secondary wave 402 reduces (as denoted at intermediate region 410) as the amplitude of the carrier wave 402 reduces (as denoted in region 412). The amplitude of the secondary wave 403 is at a maximum in the regions 414 and 416 corresponding to the maximum amplitudes of the carrier wave 402. The fluctuations in power of the faster gamma oscillations are correlated with power changes in the lower frequency band. This interaction is independent of the phases of the signals.

The brainwave 404 represents the carrier and secondary waves 402 and 403, as frequency coupled in a phase to phase manner. Given that the carrier and secondary waves 402 and 403 are aligned in phase with one another, the brainwave 404 exhibits a relatively even signal with little notable phase shift. Phase-locking occurs between oscillations at different frequencies. In each slow cycle, there are four faster cycles and their phase relationship remains fixed.

The brainwave 405 represents the carrier and secondary waves 402 and 403, as frequency coupled in a phase to power manner. For example, the amplitude of the resulting brainwave 405 is modulated based on the phase of the carrier wave 402. Accordingly, the brainwave 405 exhibits a maximum in amplitude in regions 418 which correspond to the positive 90° phase shift point (at reference numerals 420) in the carrier wave 402. The brainwave 405 exhibits a minimum amplitude in regions 422 which correspond to the negative 90° phase shift point (at reference numerals 424) in the carrier wave 402. Hence, in the example of brainwave 405, the amplitude of the higher frequency brainwave is modulated/determined by the phase of the lower frequency carrier wave.

The brain waves 406-408 reflect the carrier and secondary waves 402 and 403 when coupled in different manners, namely phase to frequency (brainwave 406), power to frequency (brainwave 407) and frequency to frequency (brainwave 408). It is recognized that the brain waves illustrated in FIGS. 4A-4G represent non-limiting examples and may be shaped in the numerous other manners. The different types of cross-frequency interaction are not mutually exclusive. For instance, the phase of theta oscillations might modulate both frequency and power of the gamma oscillations.

As explained herein, nested stimulation may be applied such that two, three or more frequency bands are coupled to one another to achieve various results. As noted above, the lower band represents a carrier wave with higher frequency bands nested on the lower carrier wave. The higher frequency bands carry content to be utilized by the targeted neural modules. For example, the high-frequency content may be superimposed into the phase of the lower carrier wave, such as in connection with external information transmission. Alternatively, the high-frequency content may be added while maintaining phase synchronization. Optionally, the high-frequency content may be added through amplitude or frequency modulation to the lower carrier wave. It is recognized that the high-frequency content may be added in other manners as well, based on the particular neural region of interest and desired effect that is being sought.

Nested stimulation according to some embodiments applies multiple frequency bands to form a stimulation waveform or pattern. The waveform may be analog waveform. Alternatively, the stimulation pattern may include discontinuous pulses in other embodiments. The frequency bands may include respective bands from an infra-slow frequencies to sigma frequencies.

The brain organization is shaped by an economic trade-off between minimizing costs and allowing efficiency in connection with adaptive structural and functional topological connectivity patterns. For example, a low-cost, but low efficiency, organization would represent a regular lattice type topology. At an opposite end of the spectrum, a random topology would be highly efficient, but be more economically costly.

Figure 5:
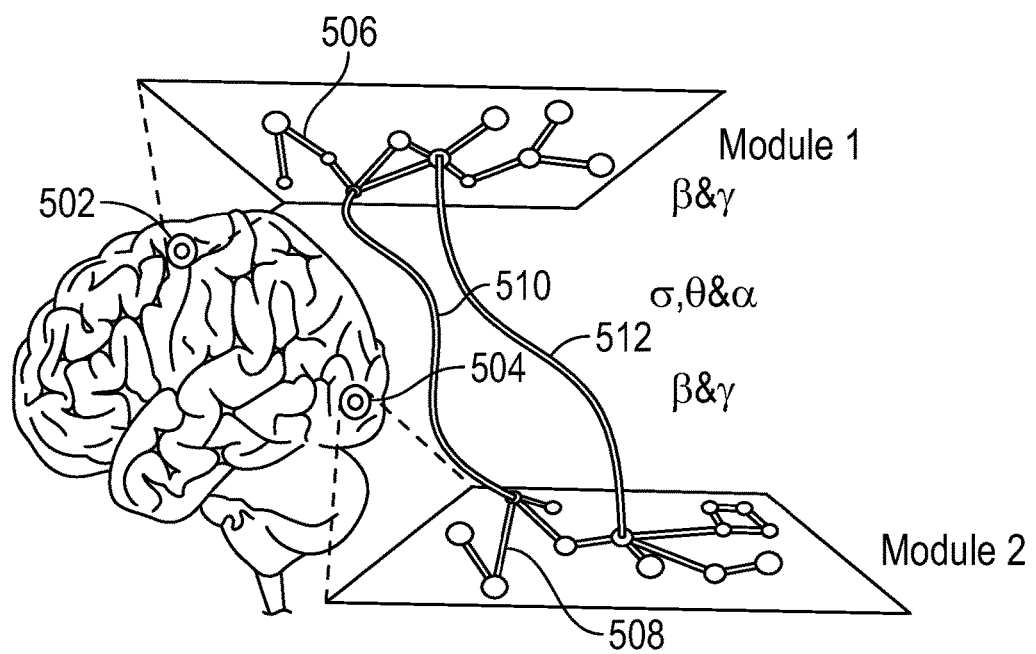
FIG. 5 illustrates a model of a portion of the brain with interest directed to neural modules in accordance with embodiments herein.

FIG. 5 illustrates a model of a portion of the brain with interest directed to neural modules 502 and 504. Local activity within modules 502 and 504 generally exhibits high frequency brain waves/oscillations (as generally denoted by the links 506 and 508). For example, the high-frequency brain waves/oscillations may represent beta and gamma waves. The neural modules 502 and 504 communicate with one another over long-distance communications links (as denoted at 510 and 512). The communications links 510, 512 between distributed neural modules 502, 504 occur through the use of low frequency brain waves (e.g. Delta, Theta and Alpha waves). The communication between modules 502, 504 utilizes nesting or cross frequency coupling between the low frequency brain waves (traveling between distributed neural modules) and the high frequency brain waves (within corresponding neural modules). In this manner, transient coherence or phase synchronization binds distributed neural assemblies/modules within the brain through dynamic (and potentially long-range) connections. Nested therapy may be utilized to facilitate long-distance communication links.

Figure 6:
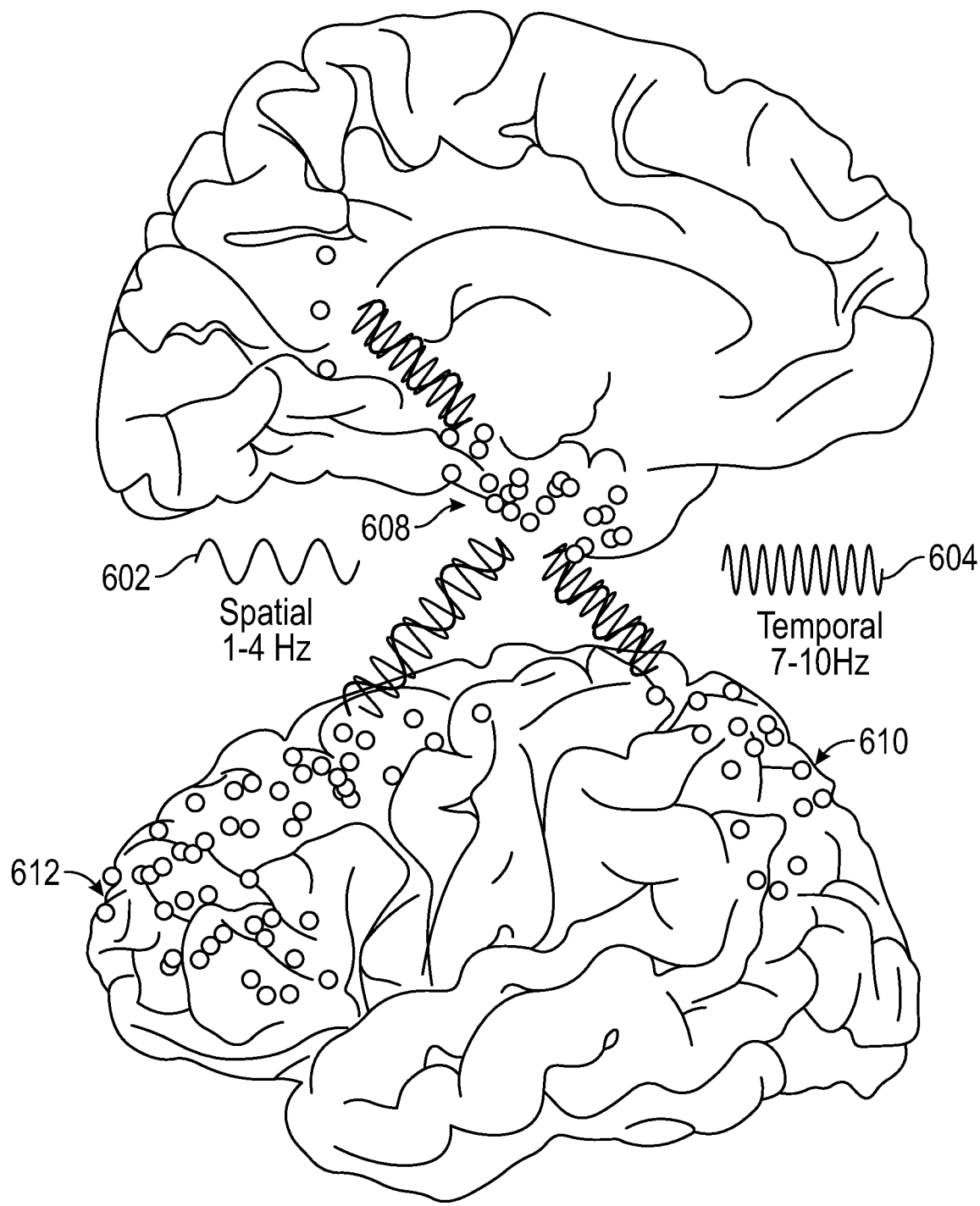
FIG. 6 illustrates a model reflecting the memory functionality of a brain in accordance with embodiments herein.

FIG. 6 illustrates a model reflecting the memory functionality of a brain. Memory has spatial and temporal characteristics 602 and 604. Memories are encoded through low frequency coupling between parahippocampal area 606, frontal area 608 and parietal (PFC) area 610. The spatial and temporal characteristics 602, 604 of memory are multiplexed along common pathways through different frequencies. For example, the spatial characteristics 602 of memory are carried within the Delta wave frequency band, while the temporal characteristics 604 of memory are carried within the theta wave frequency band. Nested therapy may be utilized to facilitate spatial and/or temporal characteristics for memories.

Figure 7A:
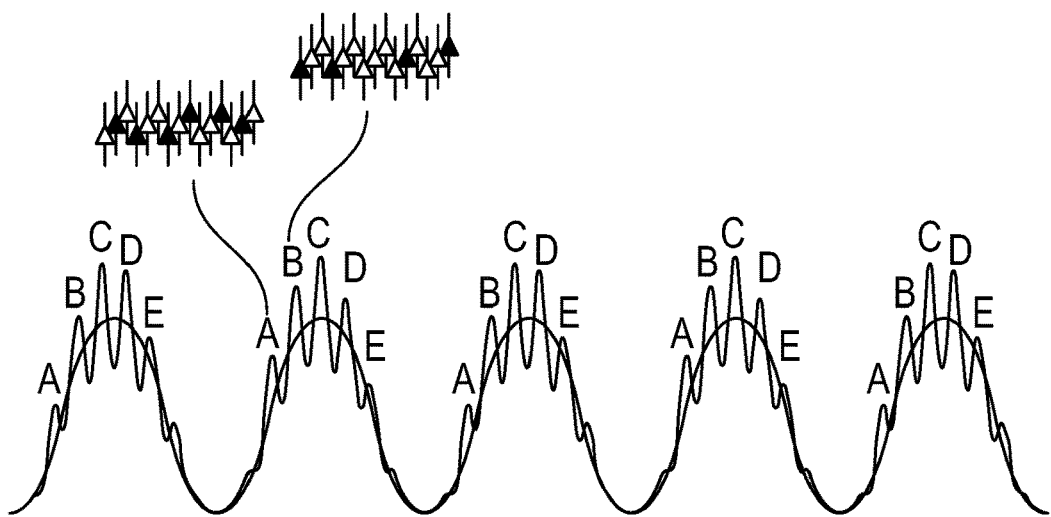
FIG. 7A illustrates models proposed, in the 2007 Jensen paper, regarding computational roles for cross-frequency interactions between theta and gamma oscillations by means of phase coding in accordance with embodiments herein.
Figure 7B:
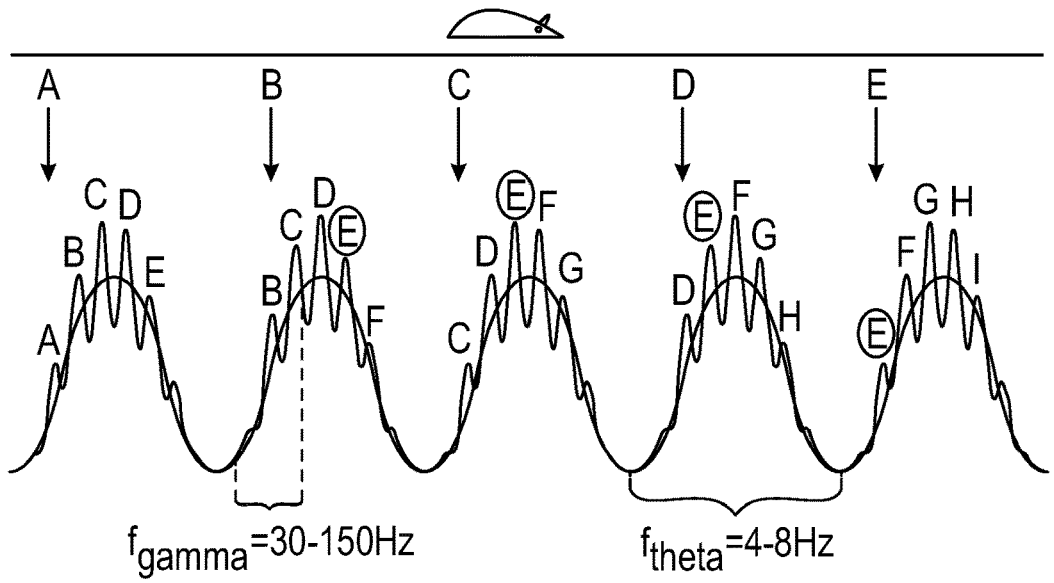
FIG. 7B illustrates models proposed, in the 2007 Jensen paper, regarding computational roles for cross-frequency interactions between theta and gamma oscillations by means of phase coding in accordance with embodiments herein.

FIGS. 7A and 7B illustrate models proposed, in the 2007 Jensen paper, regarding computational roles for cross-frequency interactions between theta and gamma oscillations by means of phase coding. FIG. 7A illustrates a model for working memory, in which individual memory representations are activated repeatedly in theta cycles. Each memory representation is represented by a subset of neurons in the network firing synchronously. Because different representations are activated in different gamma cycles, the gamma rhythm serves to keep the individual memories segmented in time. As reported by Jensen, the number of gamma cycles per theta cycle determines the span of the working memory. FIG. 7B illustrates a model accounting for theta phase precession in rats. Positional information is passed to the hippocampus, which activates the respective place cell representations and provokes the prospective recall of upcoming positions. In each theta cycle, time-compressed sequences are recalled at the rate of one representation per gamma cycle.

Figure 8A:
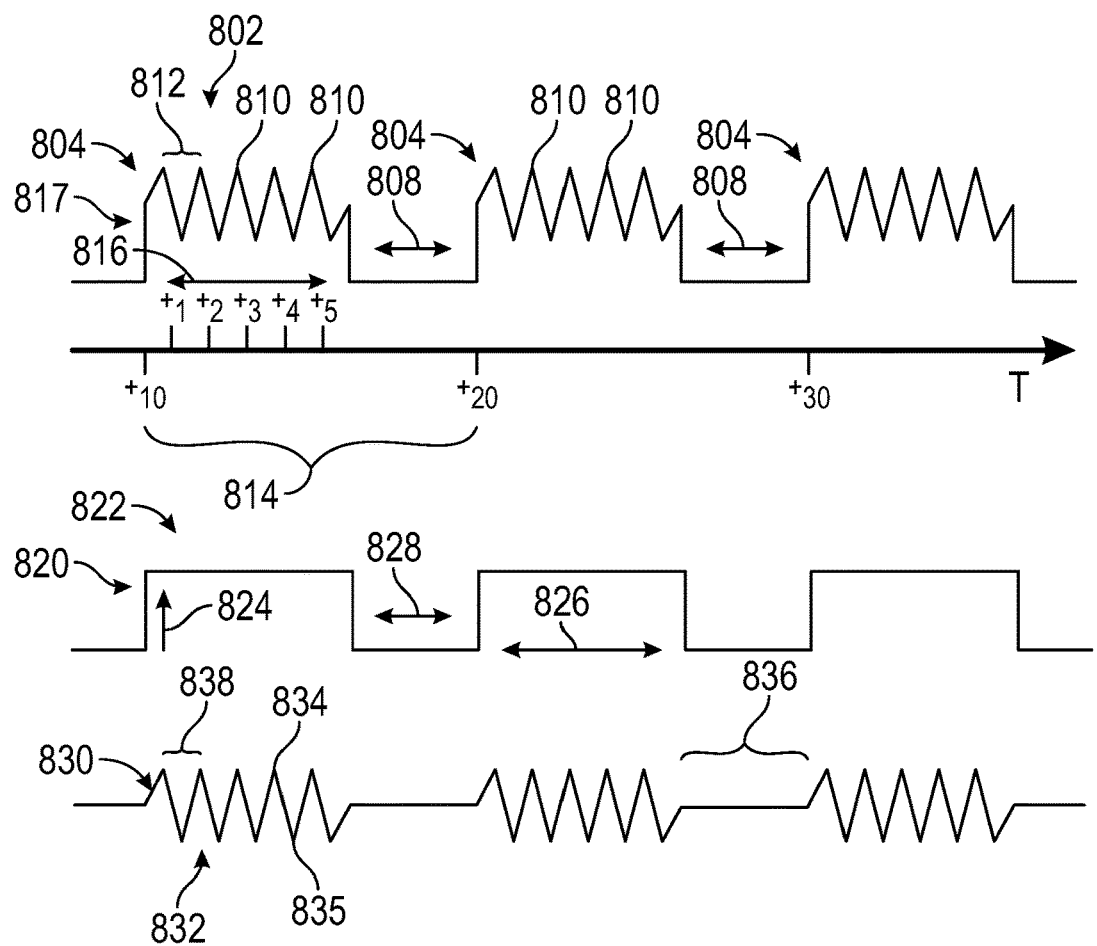
FIG. 8A illustrates an example of a nested stimulation waveform that may be delivered in connection with nested therapies to brain tissue (or brain tissue) of interest in accordance with embodiments herein.

FIG. 8A illustrates an example of a nested stimulation waveform that may be delivered in connection with nested therapies to brain tissue (or brain tissue) of interest in accordance with embodiments herein. In FIG. 8A, the nested stimulation waveform 802 includes multiple pulse bursts 804 that are separated from one another by an inter-burst delay 808. Each of the pulse bursts 804 includes a series of individual pulses or spikes 810. The pulses 810 are delivered over a burst length 816 in connection with an individual pulse bursts 804. The rate at which the individual pulses 810 are delivered within a pulse bursts 804 is determined based on a pulse rate 812 (denoted as a bracket extending between successive positive peaks of adjacent successive pulses 810).

FIG. 8A also illustrates a timeline extending along a horizontal axis with various points in time noted along the nested stimulation waveform 802. Each of the successive pulse bursts 804 are initiated at start times T10, T20 and T30, respectively. The interval between successive start times (e.g. T10 and T-20) represents the burst to burst period 814. The timeline also illustrates examples of the timing between pulses 810 within an individual pulse burst (e.g. 804). For example, pulse peak times T1-T5 are illustrated as aligned with the peak positive point of each pulse 810. The pulse rate 812 corresponds to the pulse to pulse period 814.

The nested stimulation waveform may be decomposed into at least two primary waveform components, generally denoted as a carrier waveform 820 and a high-frequency waveform 830. In accordance with embodiments herein, the high frequency waveform is defined to correspond to high frequency physiologic neural oscillations associated with the brain tissue of interest, while the low frequency waveform is defined to correspond to low frequency physiologic neural oscillations associated with the brain tissue of interest. Optionally, one of the carrier and high frequency waveforms may be defined to differ from the low and high frequency physiologic neural oscillations. For example, the high frequency waveform may be defined to correspond to a physiologic beta or gamma wave, while the carrier waveform is defined to be independent of a physiologic delta, theta or alpha wave. Alternatively, the high frequency waveform may be defined to be independent of a physiologic beta or gamma wave, while the carrier waveform is defined to correspond to a physiologic delta, theta or alpha wave.

The carrier wave 820 may represent a non-sinusoidal waveform similar to a square wave, but with only positive or only negative wave segments 822. In the example of FIG. 8A, the carrier wave 820 includes a series of positive wave segments 822 that are defined by parameters, such as a predetermined amplitude 824, segment width 826, inter segment delay 828, among other parameters. The segment width 826 corresponds to the burst length 816, while the inter segment delay 828 corresponds to the interburst delay 808. The segment amplitude 824 defines an average amplitude for each pulse burst 804.

The high-frequency waveform 830 includes a series of bursts 832. Within each burst 832, the waveform 830 oscillates periodically by switching between positive and negative amplitudes 834 and 835 at a select frequency 838. The high-frequency waveform 830 represents an intermittent waveform in that successive adjacent bursts 832 are separated by an interburst delay 836 which corresponds to the interburst delay 808 and inter segment delay 828. The high-frequency waveform 830 is defined by various parameters such as the frequency 138, amplitudes 834, 835, interburst delay 836.

The high-frequency waveform 830 is combined with the carrier waveform 820 to form the nested stimulation waveform 802. The parameters of the high-frequency and carrier waveforms 830 and 820 may be adjusted to achieve various effects. As one example, the parameters may be adjusted to achieve cross frequency coupling with neural oscillations of interest. As one example, the parameters may be adjusted to entrain neural oscillations of interest. For example, the frequency, phase and amplitude of the carrier waveform 820 may be managed to entrain neural oscillations associated with brain tissue of interest, such as tissue associated with sensory, motor or cognitive processing. The carrier waveform 820 may entrain neural oscillations to the temporal structure defined by the carrier waveform 820 such as to facilitate selective attention in connection with certain psychiatric disorders (e.g. schizophrenia, dyslexia, attention deficit/hyperactivity disorder). Additionally or alternatively, the high-frequency waveform 830 may be managed to entrain neural oscillations associated with the brain region of interest. For example, the frequency, phase, amplitude as well as other parameters may be adjusted for the high-frequency waveform 830 to obtain entrainment of the neural oscillations of interest.

The characteristics discussed herein in connection with FIG. 8A represent non-limiting examples of therapy parameters that may be varied to define different nested therapies (e.g., different carrier waveforms and different high frequency waveforms). For example, a nonlimiting list of potential therapy parameters include pulse amplitude, pulse frequency, pulse to pulse period, the number of pulses in each burst, burst length, interburst delay, the number of pulse bursts in each nested stimulation waveform and the like. The pulse bursts may include pulses having a frequency corresponding to high frequency intrinsic neural oscillations exhibited by normal/physiologic brain tissue of interest. The pulse bursts are separated from one another with a burst to burst period that corresponds to a frequency of the low-frequency intrinsic neural oscillations exhibited by normal/physiologic brain tissue of interest.

The nested stimulation waveform combines the carrier waveform and high frequency waveform in a predetermined manner. For example, the carrier and high-frequency waveforms may be combined utilizing one of the following types of cross frequency coupling: power to power; phase to power; phase to phase; phase to frequency; power to frequency and frequency to frequency. Optionally, the carrier and high-frequency waveforms are combined through phase to power cross frequency coupling, in which the phase of the carrier waveform modulates the power of the high-frequency waveform. For example, the waveforms 820 and 830 may be combined in the manners discussed herein in connection with FIGS. 4A-4G.

As one example, first parameters may be set to define the carrier waveform to correspond to physiologic neural oscillations in the theta wave frequency band, while second parameters may be set to define the high-frequency waveform to correspond to physiologic neural oscillations in the gamma wave frequency band. As explained herein, the nested stimulation waveform may be defined to entrain and modulate the neural oscillations in the gamma wave frequency band in connection with at least one of sensory, motor, and cognitive events. Optionally, the nested stimulation waveform may be managed in connection with a pattern of interest in neural oscillations through cross frequency coupling between theta and gamma waves associated with the brain tissue of interest.

As explained herein, the brain tissue of interest may correspond to one brain region or comprise distributed neural modules located in separate regions of the brain. In accordance with embodiments herein methods and systems may manage the nested stimulation waveform in connection with cross frequency coupling between neural oscillations associated with one or distributed neural modules that exhibit long-distance communication over neural oscillations within at least one of delta, theta and alpha wave frequency bands.

In accordance with embodiments herein, methods and system measure intrinsic neural oscillations, determine whether the nested stimulation waveform is achieving a desired modulation (e.g., entrainment) of the intrinsic neural oscillations, and adjust at least one of the first and second parameters to maintain the desired modulation (e.g., entrainment) of the intrinsic neural oscillations. The intrinsic neural oscillations may exhibit pathologic behavior or patterns. The nested stimulation waveform is adjusted until the intrinsic neural oscillation exhibits a physiologic behavior or pattern.

Figure 8B:
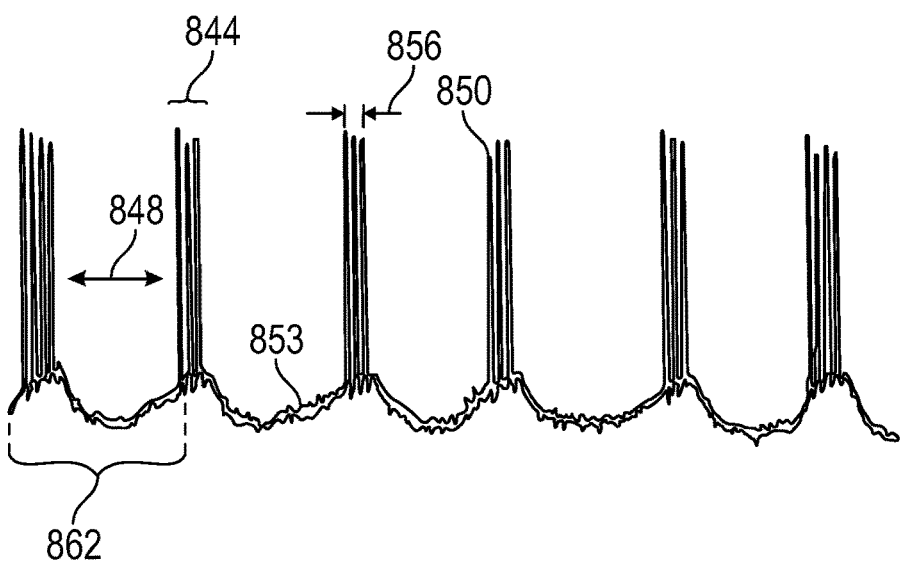
FIG. 8B illustrates an example of a nested stimulation waveform that may be delivered in connection with nested therapies to brain tissue (or brain tissue) of interest in accordance with embodiments herein.

FIG. 8B illustrates an example of a nested stimulation waveform that may be delivered in connection with nested therapies to brain tissue (or brain tissue) of interest in accordance with embodiments herein. In FIG. 8B, the nested stimulation waveform 842 includes multiple pulse bursts 844 that are separated from one another by an inter-burst delay 848. Each of the pulse burst 844 includes a series of individual pulses or spikes 850. The pulses 850 are delivered over a burst length 856 in connection with an individual pulse burst 844. The rate at which the individual pulses 850 are delivered within a pulse burst 844 is determined based on a pulse rate 862 (denoted as a bracket extending between successive positive peaks of adjacent successive pulses 810. The nested stimulation waveform 842 includes a low frequency carrier waveform 853 and a high frequency waveform that defines the characteristics of the pulses 850.

Figure 8C:
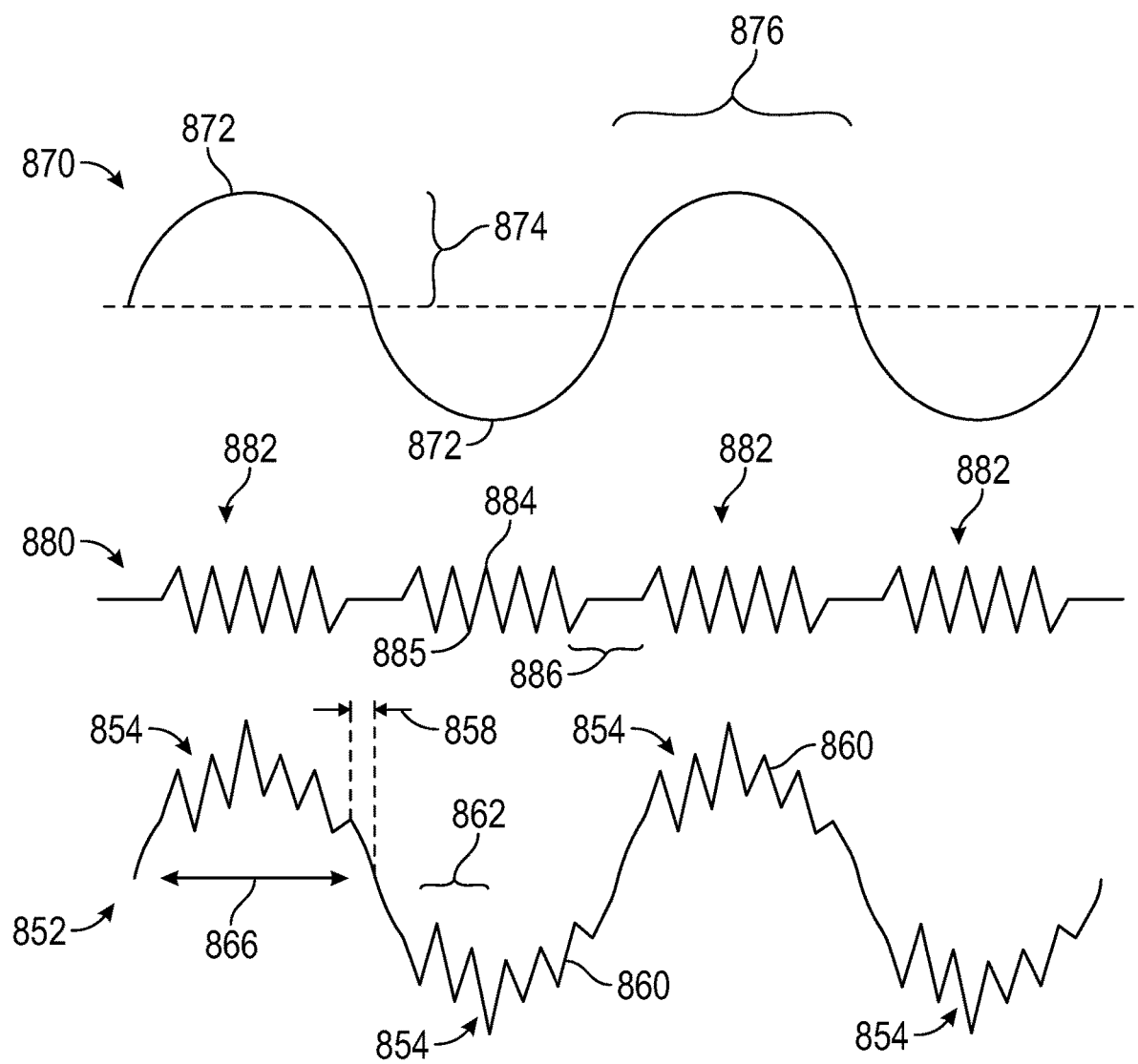
FIG. 8C illustrates an alternative example of a nested stimulation waveform that may be delivered in connection with nested therapies to brain tissue (or brain tissue) of interest in accordance with embodiments herein.
Figure 9A:
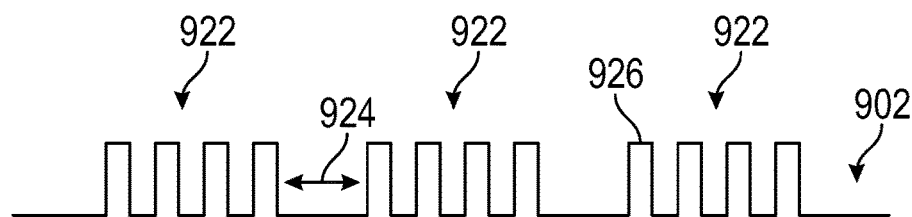
FIGS. 9A-9F illustrate alternative nested stimulation waveforms that may be utilized in accordance with embodiments herein.
Figure 9B:
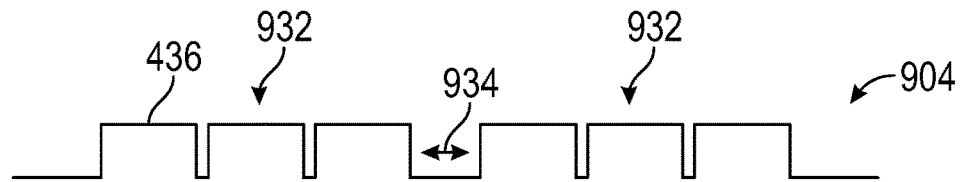
Figure 9C:
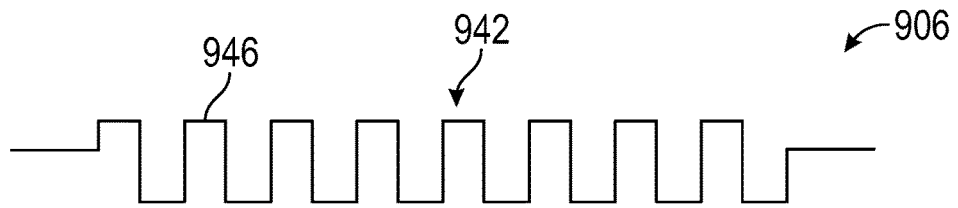
Figure 9D:
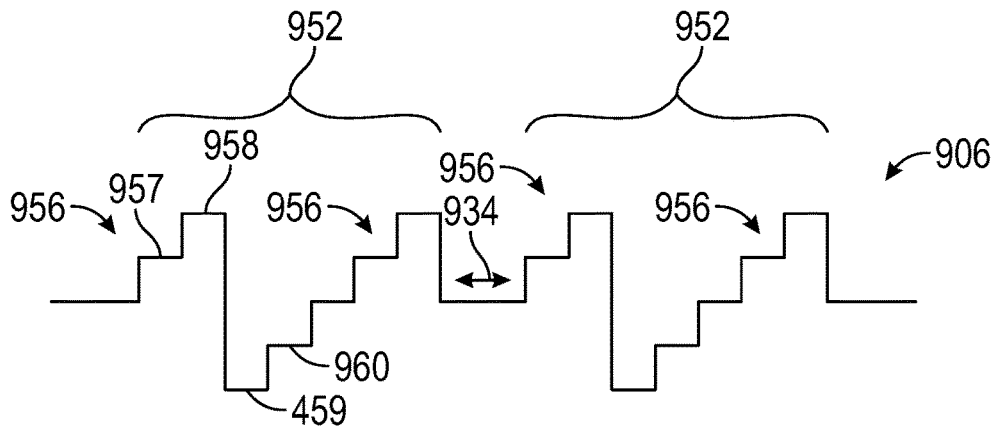
Figure 9E:
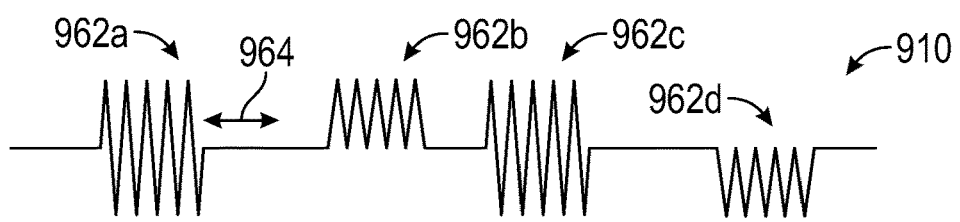
Figure 9F:
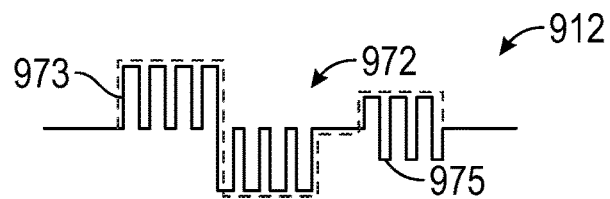

FIG. 8C illustrates an alternative example of a nested stimulation waveform that may be delivered in connection with nested therapies to brain tissue (or brain tissue) of interest in accordance with embodiments herein. In FIG. 8C, the nested stimulation waveform 852 includes multiple pulse bursts 854 that are separated from one another by an inter-burst delay 858. Each of the pulse burst 854 includes a series of individual pulses or spikes 860. The pulses 810 are delivered over a burst length 866 in connection with an individual pulse burst 854. The rate at which the individual pulses 860 are delivered within a pulse burst 854 is determined based on a pulse rate 862 (denoted as a bracket extending between successive positive peaks of adjacent successive pulses 860).

The nested stimulation waveform 852 is decomposed into a carrier waveform 870 and a high-frequency waveform 880. The carrier wave 870 may represent a sinusoidal waveform having positive and negative wave segments 872. The positive and negative wave segments 822 are defined by a predetermined amplitude 874 and segment width 876 among other parameters.

Figure 7C:
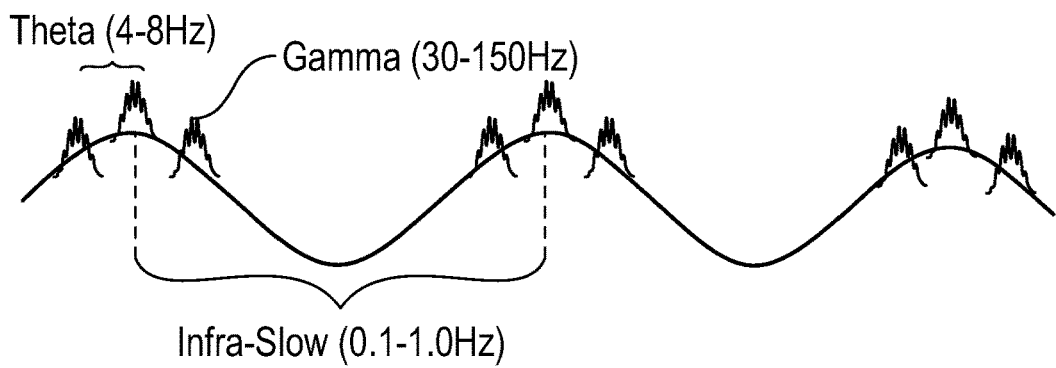
FIG. 7C illustrates cross-frequency interactions including infra-slow wave oscillations in accordance with embodiments herein.

In some embodiments, the carrier wave 870 may exhibit an infraslow frequency (less than 1 Hz, generally 0.001-1.0 Hz, and 0.01-0.1 Hz in some embodiments) as shown in, for example, FIG. 7C. In some embodiments, 0.01 Hz is employed for carrier wave 870 for electrical stimulation of one or more neuronal sites. Different infraslow frequencies may be employed to integrate Information from different resting state networks depending upon the specific neurological condition of the patient according to representative embodiments. For example, neurological disorders involving different parts of the ACC may be treated by using an infraslow frequency of 0.02 Hz according to embodiments herein. Neurological disorders involving the PCC/precuneus may be treated by using an infraslow frequency of 0.08 Hz according to embodiments herein. Neurological disorders involving the ACC and PCC/precuneus may be treated by using an infraslow frequency of 0.09-0.11 Hz according to embodiments herein.

The high-frequency waveform 880 includes a series of bursts 882. Within each burst 882, the waveform 880 oscillates periodically by switching between positive and negative amplitudes 884 and 885 at a select frequency 888. The high-frequency waveform 880 represents an intermittent waveform in that successive adjacent bursts 882 are separated by an interburst delay 886 which corresponds to the interburst delay 858.

The high-frequency waveform 880 is combined with the carrier waveform 870 to form the nested stimulation waveform 852. The parameters of the high-frequency and carrier waveforms 880 and 870 are adjusted to entrain and/or achieve cross frequency coupling with neural oscillations of interest. For example, the frequency, phase and amplitude of the carrier waveform 870 may be managed to entrain neural oscillations associated with a brain region of interest, such as a brain region associated with sensory, motor or cognitive processing. The carrier waveform 870 may entrain neural oscillations to the temporal structure defined by the carrier waveform 870 such as to facilitate selective attention in connection with certain psychiatric disorders (e.g. schizophrenia, dyslexia, attention deficit/hyperactivity disorder). Additionally or alternatively, the high-frequency waveform 880 may be managed to entrain neural oscillations associated with the brain region of interest. For example, the frequency, phase, amplitude as well as other parameters may be adjusted for the high-frequency waveform 880 to obtain entrainment of the neural oscillations of interest.

The carrier and high-frequency waveforms 870 and 880 may be combined utilizing one of the following types of cross frequency coupling: power to power; phase to power; phase to phase; phase to frequency; power to frequency and frequency to frequency. For example, the waveforms 870 and 880 may be combined in the manner discussed herein in connection with FIGS. 4A-4G. As one example, the carrier and high-frequency waveforms 870 and 880 are combined through phase to power cross frequency coupling (as illustrated in connection with the waveform 405 in FIGS. 4A-4G), in which the phase of the carrier waveform modulates the power of the high-frequency waveform.

FIGS. 9A-9F illustrate alternative nested stimulation waveforms that may be utilized in accordance with embodiments herein. The nested stimulation waveforms 902-912 may be delivered from multiple electrode combinations along the lead. The nested stimulation waveform 902 includes a carrier waveform that is cross frequency coupled to a high frequency waveform to form multiple (e.g. three) pulse bursts 922 separated by an inter-burst interval 924. The pulse burst 922 include a series of pulses 926 having a common polarity (e.g. all positive pulses or all negative pulses).

The nested stimulation waveform 904 includes a pair of pulse bursts 932 separated by an interburst interval 934. Each pulse burst 932 includes a series of pulses 936 (e.g. three) that have a common polarity. The nested stimulation waveform 906 includes a single pulse burst 942 having a series of pulses 946, each of which is bipolar (e.g. extends between positive and negative polarities). The pulses 946 have one of two states/voltage levels, namely a positive pulse amplitude and a negative pulse amplitude that are common.

The stimulation waveform 908 includes a pair of pulse bursts 952 separated by an inter-burst interval 954. Each pulse burst 952 includes multiple pulses 956 that are bipolar (extending between positive and negative polarities). The pulses 956 vary between more than two states or voltage levels, namely first and second positive voltages 957-958 and first and second negative voltages 959 and 960. Optionally, additional voltage levels/states may be utilized and the positive and negative voltage levels need not be common.

The nested stimulation waveform 910 includes pulse burst 962A-962D that are separated by an interburst interval 964. The interburst intervals 964 may differ from one another or be common. The pulse bursts 962A and 962C have similar positive and negative amplitudes, while the pulse bursts 962B (positive) and 962D (negative) are monopolar and different from one another. The nested stimulation waveform 912 illustrates a single pulse burst 972 that has a carrier wave component (as denoted by envelope 973 in dashed lines) that is modulated by a higher frequency component (as denoted by solid lines 975). Optionally, the nested stimulation waveform may be varied from the foregoing examples. Additionally, separate and distinct nested stimulation waveforms may be delivered from different electrode combinations at non-overlapping distinct points in time.

Electrical Stimulation Devices

Figure 1B:
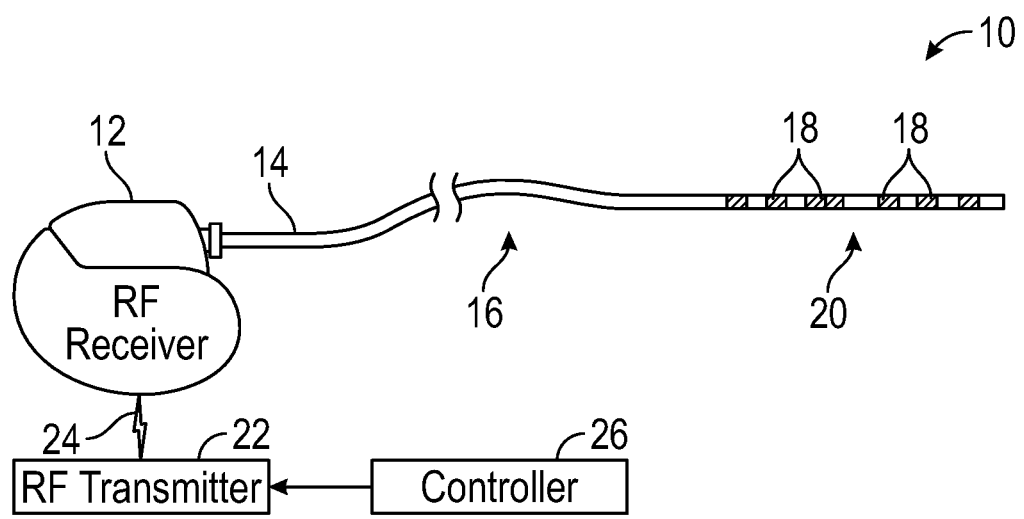
FIG. 1B illustrates an example neurological stimulation (NS) systems for electrically stimulating a predetermined site area to treat one or more neurological disorders or conditions in accordance with embodiments herein.

FIGS. 1A-1B Illustrate example neurological stimulation (NS) systems 10 for electrically stimulating a predetermined site area to treat one or more neurological disorders or conditions. In general terms, stimulation system 10 includes an implantable pulse generating source or electrical IMD 12 (generally referred to as an "implantable medical device" or "IMD") and one or more implantable electrodes or electrical stimulation leads 14 for applying nested stimulation pulses to a predetermined site. In operation, both of these primary components are implanted in the person's body, as discussed below. In certain embodiments, IMD 12 is coupled directly to a connecting portion 16 of stimulation lead 14. In some embodiments, IMD 12 is incorporated into the stimulation lead 14 and IMD 12 instead is embedded within stimulation lead 14. For example, such a stimulation system 10 may be a Bion® stimulation system manufactured by Advanced Bionics Corporation. Whether IMD 12 is coupled directly to or embedded within the stimulation lead 14, IMD 12 controls the stimulation pulses transmitted to one or more stimulation electrodes 18 located on a stimulating portion 20 of stimulation lead 14, positioned in communication with a predetermined site, according to suitable therapy parameters (e.g., duration, amplitude or intensity, frequency, pulse width, firing delay, etc.).

As contemplated in embodiments herein, a predetermined stimulation site for tissue of interest can include either peripheral neuronal tissue and/or central neuronal tissue. Neuronal tissue includes any tissue associated with the peripheral nervous system or the central nervous system. Peripheral neuronal tissue can include a nerve root or root ganglion or any neuronal tissue that lies outside the brain, brainstem or spinal cord. Peripheral nerves can include, but are not limited to olfactory nerve, optic, nerve, oculomotor nerve, trochlear nerve, trigeminal nerve, abducens nerve, facial nerve, vestibulocochlear (auditory) nerve, glossopharyngeal nerve, vagal nerve, accessory nerve, hypoglossal nerve, suboccpital nerve, the greater occipital nerve, the lesser occipital nerve, the greater auricular nerve, the lesser auricular nerve, the phrenic nerve, brachial plexus, radial axillary nerves, musculocutaneous nerves, radial nerves, ulnar nerves, median nerves, intercostal nerves, lumbosacral plexus, sciatic nerves, common peroneal nerve, tiblal nerves, sural nerves, femoral nerves, gluteal nerves, thoracic spinal nerves, obturator nerves, digital nerves, pudendal nerves, plantar nerves, saphenous nerves, ilioinguinal nerves, gentofemoral nerves, and iliohypogastric nerves.

Central neuronal tissue includes brain tissue, spinal tissue or brainstem tissue. Brain tissue can include thalamus/subthalamus, basal ganglia, hippocampus, amygdala, hypothalamus, mammilary bodies, substantia nigra or cortex or white matter tracts afferent to or efferent from the above-mentioned brain tissue, inclusive of the corpus callosum. Spinal tissue can include the ascending and descending tracts of the spinal cord, more specifically, the ascending tracts of that comprise intralaminar neurons or the dorsal column. The brainstem tissue can include the medulla oblongata, pons or mesencephalon, more particular the posterior pons or posterior mesencephalon, Lushka's foramen, and ventrolateral part of the medulla oblongata.

A doctor, the patient, or another user of IMD 12 may directly or in directly input therapy parameters to specify or modify the nature of the stimulation provided.

In FIG. 1B, the IMD 12 includes an implantable wireless receiver. An example of a wireless receiver may be one manufactured by Advanced Neuromodulation Systems, Inc., such as the Renew® System, part numbers 3408 and 3416. In another embodiment, the IMD can be optimized for high frequency operation as described in U.S. Provisional Application Ser. No. 60/685,036, filed May 26, 2005, entitled "SYSTEMS AND METHODS FOR USE IN PULSE GENERATION," which is incorporated herein by reference. The wireless receiver is capable of receiving wireless signals from a wireless transmitter 22 located external to the person's body. The wireless signals are represented in FIG. 1B by wireless link symbol 24. A doctor, the patient, or another user of IMD 12 may use a controller 26 located external to the person's body to provide control signals for operation of IMD 12. Controller 26 provides the control signals to wireless transmitter 22, wireless transmitter 22 transmits the control signals and power to the wireless receiver of IMD 12, and IMD 12 uses the control signals to vary the signal parameters of electrical signals transmitted through electrical stimulation lead 14 to the stimulation site. Thus, the external controller 26 can be for example, a handheld programmer, to provide a means for programming the IMD. An example wireless transmitter may be one manufactured by Advanced Neuromodulation Systems, Inc., such as the Renew® System, part numbers 3508 and 3516.

The IMD 12 applies burst stimulation to brain tissue of a patient. Specifically, the IMD includes a microprocessor and a pulse generation module. The pulse generation module generates the electrical pulses according to a defined pulse width and pulse amplitude and applies the electrical pulses to defined electrodes. The microprocessor controls the operations of the pulse generation module according to software instructions stored in the device.

The IMD 12 can be adapted by programming the microprocessor to deliver a number of spikes (relatively short pulse width pulses) that are separated by an appropriate interspike interval. Thereafter, the programming of the microprocessor causes the pulse generation module to cease pulse generation operations for an interburst interval. The programming of the microprocessor also causes a repetition of the spike generation and cessation of operations for a predetermined number of times. After the predetermined number of repetitions has been completed within a nested stimulation waveform, the microprocessor can cause burst stimulation to cease for an amount of time (and resume thereafter). Also, in some embodiments, the microprocessor could be programmed to cause the pulse generation module to deliver a hyperpolarizing pulse before the first spike of each group of multiple spikes.

The microprocessor can be programmed to allow the various characteristics of the burst stimulus to be set by a physician to allow the burst stimulus to be optimized for a particular pathology of a patient. For example, the spike amplitude, the interspike interval, the interburst interval, the number of bursts to be repeated in succession, the electrode combinations, the firing delay between nested stimulation waveforms delivered to different electrode combinations, the amplitude of the hyperpolarizing pulse, and other such characteristics could be controlled using respective parameters accessed by the microprocessor during burst stimulus operations. These parameters could be set to desired values by an external programming device via wireless communication with the implantable neuromodulation device.

In representative embodiments, IMD 12 applies electrical stimulation according to a suitable noise signal (white noise, pink noise, brown noise, etc.). Details regarding implementation of a suitable noise signal can be found in U.S. Pat. No. 8,682,441, which is incorporated herein by reference In another embodiment, the IMD 12 can be implemented to apply burst stimulation using a digital signal processor and one or several digital-to-analog converters. The burst stimulus waveform could be defined in memory and applied to the digital-to-analog converter(s) for application through electrodes of the medical lead. The digital signal processor could scale the various portions of the waveform in amplitude and within the time domain (e.g., for the various intervals) according to the various burst parameters.

Figure 1C:
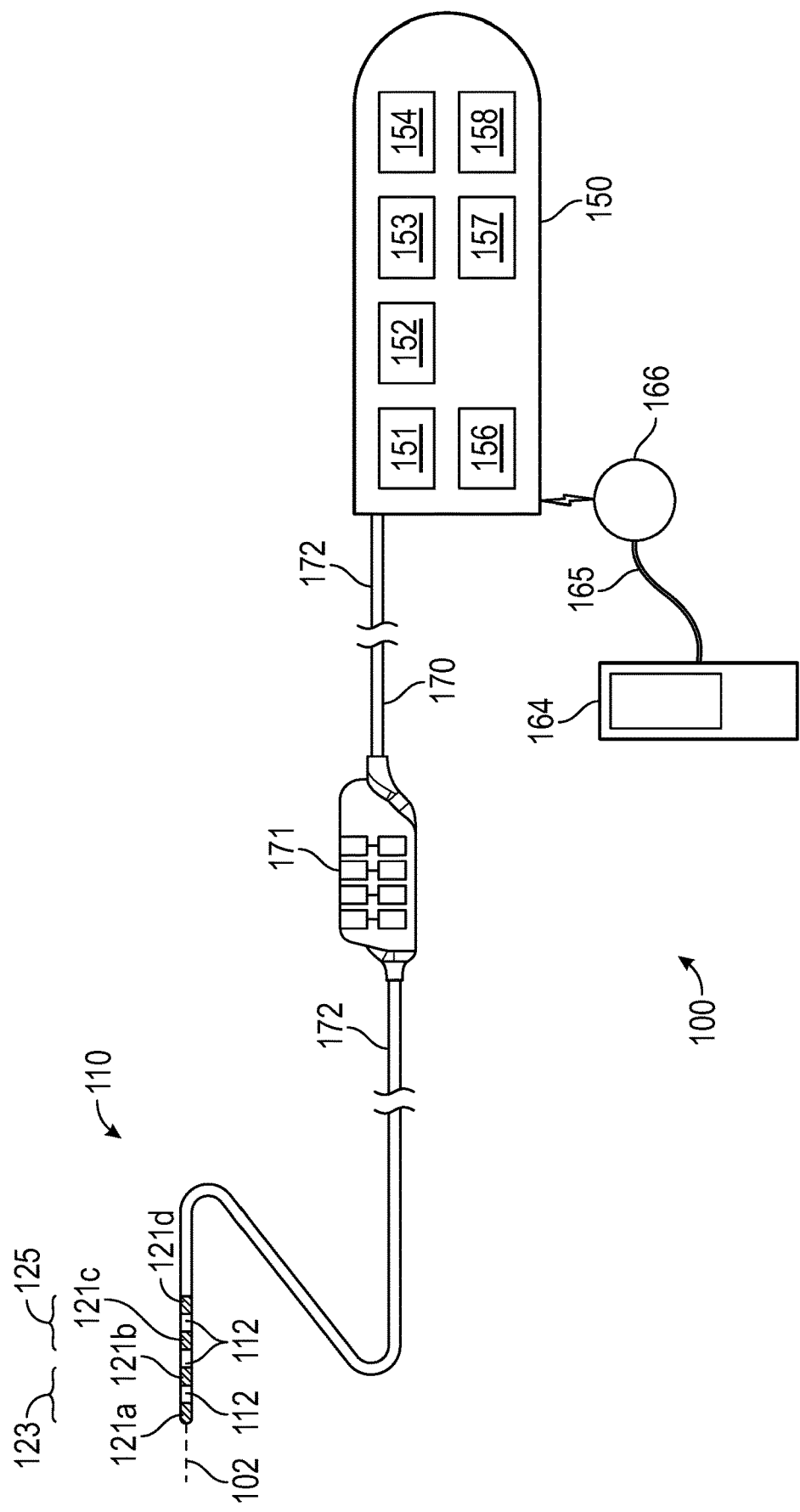
FIG. 1C depicts an NS system that delivers stimulation therapies in accordance with embodiments herein.
Figure 2A:
FIG. 2A illustrates example stimulation leads that may be used for electrically stimulating the predetermined site to treat one or more neurological disorders or conditions in accordance with embodiments herein.
Figure 2B:
FIG. 2B illustrates example stimulation leads that may be used for electrically stimulating the predetermined site to treat one or more neurological disorders or conditions in accordance with embodiments herein.
Figure 2C:
FIG. 2C illustrates example stimulation leads that may be used for electrically stimulating the predetermined site to treat one or more neurological disorders or conditions in accordance with embodiments herein.
Figure 2D:
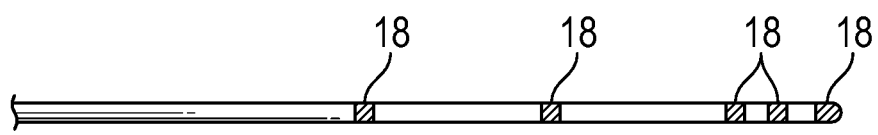
FIG. 2D illustrates example stimulation leads that may be used for electrically stimulating the predetermined site to treat one or more neurological disorders or conditions in accordance with embodiments herein.
Figure 2E:
FIG. 2E illustrates example stimulation leads that may be used for electrically stimulating the predetermined site to treat one or more neurological disorders or conditions in accordance with embodiments herein.
Figure 2F:
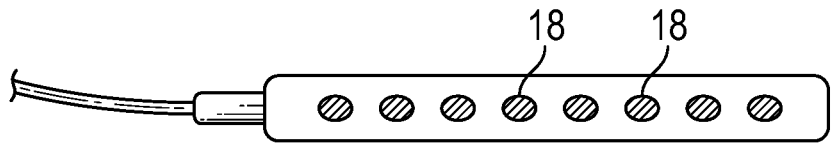
FIG. 2F illustrates example stimulation leads that may be used for electrically stimulating the predetermined site to treat one or more neurological disorders or conditions in accordance with embodiments herein.
Figure 2G:
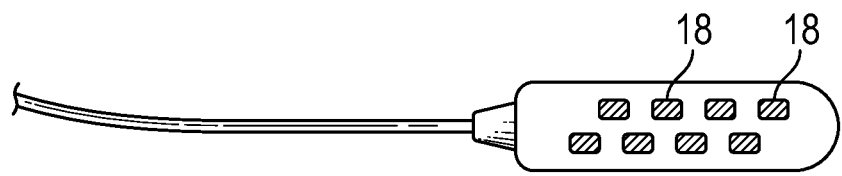
FIG. 2G illustrates example stimulation leads that may be used for electrically stimulating the predetermined site to treat one or more neurological disorders or conditions in accordance with embodiments herein.
Figure 2H:
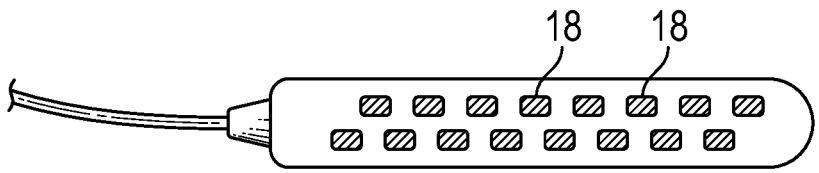
FIG. 2H illustrates example stimulation leads that may be used for electrically stimulating the predetermined site to treat one or more neurological disorders or conditions in accordance with embodiments herein.
Figure 2I:
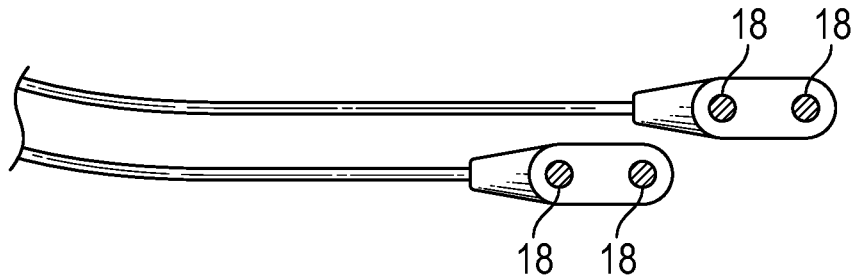
FIG. 2I illustrates example stimulation leads that may be used for electrically stimulating the predetermined site to treat one or more neurological disorders or conditions in accordance with embodiments herein.

FIG. 1C depicts an NS system 100 that delivers stimulation therapies in accordance with embodiments herein. For example, the NS system 100 may be adapted to stimulate spinal cord tissue, peripheral nervous tissue, deep brain tissue, or any other suitable nervous/brain tissue of interest within a patient's body.

The NS system 100 may be controlled to deliver various types of nested stimulation therapy, such as high frequency neurostimulation therapies, burst neurostimulation therapies and the like. High frequency neurostimulation includes a continuous series of monophasic or biphasic pulses that are delivered at a predetermined frequency. Burst neurostimulation includes short sequences of monophasic or biphasic pulses, where each sequence is separated by a quiescent period. In general, nested therapies include a continuous, repeating or intermittent pulse sequence delivered at a frequency and amplitude configured to avoid inducing (or introduce a very limited) paresthesia.

The NS system 100 may deliver nested stimulation therapy based on preprogrammed therapy parameters. The therapy parameters may include, among other things, pulse amplitude, pulse polarity, pulse width, pulse frequency, interpulse interval, inter burst interval, electrode combinations, firing delay and the like. Optionally, the NS system 100 may represent a closed loop neurostimulation device that is configured to provide real-time sensing functions from a lead. The configuration of the lead sensing electrodes may be varied depending on the neuronal anatomy of the sensing site(s) of interest. The size and shape of electrodes is varied based on the implant location. The electronic components within the NS system 100 are designed with both stimulation and sensing capabilities, including alternative nested stimulation therapy, such as burst mode, high frequency mode and the like.

The NS system 100 includes an implantable medical device (IMD) 150 that is adapted to generate electrical pulses for application to tissue of a patient. The IMD 150 typically comprises a metallic housing or can 158 that encloses a controller 151, pulse generating circuitry 152, a charge storage circuit 153, a battery 154, a far-field and/or near field communication circuitry 155, battery charging circuitry 156, switching circuitry 157, memory 158 and the like. The charge storage circuit 153 may represent one or more capacitors and/or battery cells that store charge used to produce the therapies described herein. The pulse generating circuitry 152, under control of the controller 151, manages discharge of the charge storage circuit 153 to shape the morphology of the waveform delivered while discharging energy. The switching circuitry 157 connects select combinations of the electrodes 121a-d to the pulse generating circuitry 152 thereby directing the stimulation waveform to a desired electrode combination. As explained herein, the switching circuitry 157 successively connects the pulse generating circuitry 152 to successive electrode combinations 123 and 125. The components 151-158 are also within the IMD 12 (FIGS. 1A and 1B).

The controller 151 typically includes one or more processors, such as a microcontroller, for controlling the various other components of the device. Software code is typically stored in memory of the IMD 150 for execution by the microcontroller or processor to control the various components of the device.

The IMD 150 may comprise a separate or an attached extension component 170. If the extension component 170 is a separate component, the extension component 170 may connect with the "header" portion of the IMD 150 as is known in the art. If the extension component 170 is integrated with the IMD 150, internal electrical connections may be made through respective conductive components. Within the IMD 150, electrical pulses are generated by the pulse generating circuitry 152 and are provided to the switching circuitry 157. The switching circuitry 157 connects to outputs of the IMD 150. Electrical connectors (e.g., "Bal-Seal" connectors) within the connector portion 171 of the extension component 170 or within the IMD header may be employed to conduct various stimulation pulses. The terminals of one or more leads 110 are inserted within connector portion 171 or within the IMD header for electrical connection with respective connectors. Thereby, the pulses originating from the IMD 150 are provided to the lead 110. The pulses are then conducted through the conductors of the lead 110 and applied to tissue of a patient via stimulation electrodes 121a-d that are coupled to blocking capacitors. Any suitable known or later developed design may be employed for connector portion 171.

The stimulation electrodes 121a-d may be positioned along a horizontal axis 102 of the lead 110, and are angularly positioned about the horizontal axis 102 so the stimulation electrodes 121a-d do not overlap. The stimulation electrodes 121a-d may be in the shape of a ring such that each stimulation electrode 121a-d continuously covers the circumference of the exterior surface of the lead 110. Adjacent stimulation electrodes 121a-d are separated from one another by non-conducting rings 112, which electrically isolate each stimulation electrode 121a-d from an adjacent stimulation electrode 121a-d. The non-conducting rings 112 may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The stimulation electrodes 121a-d may be configured to emit the pulses in an outward radial direction proximate to or within a stimulation target. Additionally or alternatively, the stimulation electrodes 121a-d may be in the shape of a split or non-continuous ring such that the pulse may be directed in an outward radial direction adjacent to the stimulation electrodes 121a-d. The stimulation electrodes 121a-d deliver tonic, high frequency and/or burst nested stimulation waveforms as described herein. Optionally, the electrodes 121a-d may also sense neural oscillations and/or sensory action potential (neural oscillation signals) for a data collection window.

The lead 110 may comprise a lead body 172 of insulative material about a plurality of conductors within the material that extend from a proximal end of lead 110, proximate to the IMD 150, to its distal end. The conductors electrically couple a plurality of the stimulation electrodes 121 to a plurality of terminals (not shown) of the lead 110. The terminals are adapted to receive electrical pulses and the stimulation electrodes 121a-d are adapted to apply the pulses to the stimulation target of the patient. Also, sensing of physiological signals may occur through the stimulation electrodes 121a-d, the conductors, and the terminals. It should be noted that although the lead 110 is depicted with four stimulation electrodes 121a-d, the lead 110 may include any suitable number of stimulation electrodes 121a-d (e.g., less than four, more than four) as well as terminals, and internal conductors. Additionally or alternatively, various sensors (e.g., a position detector, a radiopaque fiducial) may be located near the distal end of the lead 110 and electrically coupled to terminals through conductors within the lead body 172.

Although not required for any embodiments, the lead body 172 of the lead 110 may be fabricated to flex and elongate upon implantation or advancing within the tissue (e.g., nervous tissue) of the patient towards the stimulation target and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile.

By way of example, the IMD 12, 150 may include a processor and associated charge control circuitry as described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IMD using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference. An example and discussion of "constant current" pulse generating circuitry (e.g., pulse generating circuitry 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IMD 12, 150. Different burst and/or high frequency pulses on different stimulation electrodes may be generated using a single set of the pulse generating circuitry using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., tonic stimulation waveform, burst stimulation waveform) that include generated and delivered stimulation pulses through various stimulation electrodes of one or more leads as is also known in the art. Various sets of parameters may define the pulse characteristics and pulse timing for the pulses applied to the various stimulation electrodes. Although constant current pulse generating circuitry is contemplated for some embodiments, any other suitable type of pulse generating circuitry may be employed such as constant voltage pulse generating circuitry.

The controller 151 delivers a nested stimulation waveform to at least one electrode combination located proximate to nervous tissue of Interest, the nested stimulation waveform including a series of pulses configured to excite the nested C-fibers of the nervous tissue of interest, the nested stimulation waveform defined by therapy parameters. The controller 151 may deliver the nested stimulation waveform based on preprogrammed therapy parameters. The preprogrammed therapy parameters may be set based on information collected from numerous past patients and/or test performed upon an individual patient during initial implant and/or during periodic checkups.

Optionally, the controller 151 senses intrinsic neural oscillations from at least one electrode on the lead. Optionally, the controller 151 analyzes the intrinsic neural oscillations signals to obtain brain activity data. The controller 151 determines whether the activity data satisfies a criteria of interest. The controller 151 adjusts at least one of the therapy parameters to change the nested stimulation waveform when the activity data does not satisfy the criteria of interest. The controller 151 iteratively repeats the delivering operations for a group of TPS. The IMD selects a candidate TPS from the group of TPS based on a criteria of interest. The therapy parameters define at least one of a burst stimulation waveform or a high frequency stimulation waveform. The controller 151 may repeat the delivering, sensing and adjusting operations to optimize the nested stimulation waveform. The analyzing operation may include analyzing a feature of interest from a morphology of the neural oscillation signal over time, counting a number of occurrences of the feature of interest that occur within the signal over a predetermined duration, and generating the activity data based on the number of occurrences of the feature of interest.

Memory 158 stores software to control operation of the controller 151 for nested stimulation therapy as explained herein. The memory 158 also stores neural oscillation signals, therapy parameters, neural oscillation activity level data, sensation scales and the like. For example, the memory 158 may save neural oscillation activity level data for various different therapies as applied over a short or extended period of time. A collection of neural oscillation activity level data is accumulated for different therapies and may be compared to identify high, low and acceptable amounts of sensory activity.

A controller device 160 may be implemented to charge/recharge the battery 154 of the IMD 150 (although a separate recharging device could alternatively be employed) and to program the IMD 150 on the pulse specifications while implanted within the patient. Although, in alternative embodiments separate programmer devices may be employed for charging and/or programming the NS system 100. The controller device 160 may be a processor-based system that possesses wireless communication capabilities. Software may be stored within a non-transitory memory of the controller device 160, which may be executed by the processor to control the various operations of the controller device 160. A "wand" 165 may be electrically connected to the controller device 160 through suitable electrical connectors (not shown). The electrical connectors may be electrically connected to a telemetry component 166 (e.g., inductor coil, RF transceiver) at the distal end of wand 165 through respective wires (not shown) allowing bi-directional communication with the IMD 150. Optionally, in some embodiments, the wand 165 may comprise one or more temperature sensors for use during charging operations.

The user may initiate communication with the IMD 150 by placing the wand 165 proximate to the NS system 100. Preferably, the placement of the wand 165 allows the telemetry system of the wand 165 to be aligned with the far-field and/or near field communication circuitry 155 of the IMD 150. The controller device 160 preferably provides one or more user interfaces 168 (e.g., touchscreen, keyboard, mouse, buttons, or the like) allowing the user to operate the IMD 150. The controller device 160 may be controlled by the user (e.g., doctor, clinician) through the user interface 168 allowing the user to interact with the IMD 150. The user interface 168 may permit the user to move electrical stimulation along and/or across one or more of the lead(s) 110 using different stimulation electrode 121 combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference.

Also, the controller device 160 may permit operation of the IMD 12, 150 according to one or more therapies to treat the patient. Each therapy may include one or more sets of stimulation parameters of the pulse including pulse amplitude, pulse width, pulse frequency or inter-pulse period, firing delay, pulse repetition parameter (e.g., number of times for a given pulse to be repeated for respective stimset during execution of program), biphasic pulses, monophasic pulses, etc. The IMD 150 modifies its internal parameters in response to the control signals from the controller device 160 to vary the stimulation characteristics of the stimulation pulses transmitted through the lead 110 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

FIGS. 2A-2I illustrate example stimulation leads 14 that may be used for electrically stimulating the predetermined site to treat one or more neurological disorders or conditions. As described above, each of the one or more stimulation leads 14 incorporated in stimulation systems 10, 100 includes one or more stimulation electrodes 18 adapted to be positioned in communication with the predetermined site and used to deliver the stimulation pulses received from IMD 12 (or pulse generating circuitry 157 in FIG. 1C). A percutaneous stimulation lead 14 (corresponding to the lead 110 in FIG. 1C), such as example stimulation leads 14a-d, includes one or more circumferential electrodes 18 spaced apart from one another along the length of stimulating portion 20 of stimulation lead 14. Circumferential electrodes 18 emit electrical stimulation energy generally radially (e.g., generally perpendicular to the axis of stimulation lead 14) in all directions. A laminotomy, paddle, or surgical stimulation lead 14, such as example stimulation leads 14e-i, includes one or more directional stimulation electrodes 18 spaced apart from one another along one surface of stimulation lead 14. Directional stimulation electrodes 18 emit electrical stimulation energy in a direction generally perpendicular to the surface of stimulation lead 14 on which they are located. Although various types of stimulation leads 14 are shown as examples, embodiments herein contemplate stimulation system 10 including any suitable type of stimulation lead 14 in any suitable number. In addition, stimulation leads 14 may be used alone or in combination. For example, medial or unilateral stimulation of the predetermined site may be accomplished using a single electrical stimulation lead 14 implanted in communication with the predetermined site in one side of the head, while bilateral electrical stimulation of the predetermined site may be accomplished using two stimulation leads 14 implanted in communication with the predetermined site in opposite sides of the head.

In one embodiment, the stimulation source is transcutaneously in communication with the electrical stimulation lead. In "transcutaneous" electrical nerve stimulation (TENS), the stimulation source is external to the patient's body, and may be worn in an appropriate fanny pack or belt, and the electrical stimulation lead is in communication with the stimulation source, either remotely or directly. In another embodiment, the stimulation is percutaneous. In "percutaneous" electrical nerve stimulation (PENS), needles are inserted to an appropriate depth around or immediately adjacent to a predetermined stimulation site, and then stimulated.

The IMD 12, 150 allow each electrode of each lead to be defined as a positive, a negative, or a neutral polarity. For each electrode combination (e.g., the defined polarity of at least two electrodes having at least one cathode and at least one anode), an electrical signal can have at least a definable amplitude (e.g., voltage), pulse width, and frequency, where these variables may be independently adjusted to finely select the sensory transmitting brain tissue required to inhibit transmission of neuronal signals. Generally, amplitudes, pulse widths, and frequencies are determinable by the capabilities of the neurostimulation systems, which are known by those of skill in the art. Voltages that may be used can include, for example about 0.5 to about 10 volts, more preferably about 1 to about 10 volts.

In embodiments herein, the therapy parameter of signal frequency is varied to achieve a burst type rhythm, or burst mode stimulation. Generally, the burst stimulus frequency may be in the range of about 0.01 Hz to about 100 Hz, more particular, in the range of about 1 Hz to about 12 Hz, and more particularly, in the range of about 1 Hz to about 4 Hz, 4 Hz to about 7 Hz or about 8 Hz to about 12 Hz for each burst. Each burst stimulus comprises at least two spikes, for example, each burst stimulus can comprise about 2 to about 100 spikes, more particularly, about 2 to about 10 spikes. Each spike can comprise a frequency in the range of about 50 Hz to about 1000 Hz, more particularly, in the range of about 200 Hz to about 500 Hz. The frequency for each spike within a burst can be variable, thus it is not necessary for each spike to contain similar frequencies, e.g., the frequencies can vary in each spike. The inter-spike interval can be also vary, for example, the inter-spike interval, can be about 0.1 milliseconds to about 100 milliseconds or any range there between.

The burst stimulus is followed by an inter-burst interval, during which substantially no stimulus is applied. The inter-burst interval has duration in the range of about 1 milliseconds to about 5 seconds, more preferably, 10 milliseconds to about 300 milliseconds. It is envisioned that the burst stimulus has a duration in the range of about 1 milliseconds to about 5 seconds, more particular, in the range of about 250 msec to 1000 msec (1-4 Hz burst firing), 145 msec to about 250 msec (4-7 Hz,), 145 msec to about 80 msec (8-12 Hz) or 1 to 5 seconds in plateau potential firing. The burst stimulus and the inter-burst interval can have a regular pattern or an irregular pattern (e.g., random or irregular harmonics). More specifically, the burst stimulus can have a physiological pattern or a pathological pattern. Additional details regarding burst stimulation may be found in U.S. Pat. No. 8,897,870, which is incorporated herein by reference.

It is envisaged that the patient will require intermittent assessment with regard to patterns of stimulation. Different electrodes on the lead can be selected by suitable computer programming, such as that described in U.S. Pat. No. 5,938,690, which is incorporated by reference here in full. Utilizing such a program allows an optimal stimulation pattern to be obtained at minimal voltages. This ensures a longer battery life for the implanted systems.

FIGS. 2A-2I respectively depict stimulation portions for inclusion at the distal end of lead. Stimulation portion depicts a conventional stimulation portion of a "percutaneous" lead with multiple ring electrodes. Stimulation portion depicts a stimulation portion including several segmented electrodes. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portion includes multiple planar electrodes on a paddle structure.

A. Deep Brain Stimulation

In certain embodiments, for example, patients may have an electrical stimulation lead or electrode implanted into the brain. The anatomical targets or predetermined site may be stimulated directly or affected through stimulation in another region of the brain.

In embodiments herein, the predetermined site or implant sites include, but are not limited to thalamus/sub-thalamus, basal ganglia, hippocampus, amygdala, hypothalamus, mammilary bodies, substantia nigra or cortex or white matter tracts afferent to or efferent from the abovementioned brain tissue, inclusive of the corpus callosum. Still further, the predetermined site may comprise the auditory cortex and/or somatosensory cortex in which the stimulation devices is implanted cortically.

Once electrical stimulation lead 14, 110 has been positioned in the brain, lead 14, 110 is uncoupled from any stereotactic equipment present, and the cannula and stereotactic equipment are removed. Where stereotactic equipment is used, the cannula may be removed before, during, or after removal of the stereotactic equipment. Connecting portion 16 of electrical stimulation lead 14, 110 is laid substantially flat along the skull. Where appropriate, any burr hole cover seated in the burr hole may be used to secure electrical stimulation lead 14, 110 in position and possibly to help prevent leakage from the burr hole and entry of contaminants into the burr hole.

Once electrical stimulation lead 14, 110 has been inserted and secured, connecting portion of lead 14, 110 extends from the lead insertion site to the implant site at which IMD 12, 150 is implanted. The implant site is typically a subcutaneous pocket formed to receive and house IMD 12, 150. The implant site is usually positioned a distance away from the insertion site, such as near the chest, below the clavicle or alternatively near the buttocks or another place in the torso area. Once all appropriate components of stimulation system 10, 100 are implanted, these components may be subject to mechanical forces and movement in response to movement of the person's body. A doctor, the patient, or another user of IMD 12, 150 may directly or in directly input signal parameters for controlling the nature of the electrical stimulation provided.

Although example steps are illustrated and described, embodiments herein contemplate two or more steps taking place substantially simultaneously or in a different order. In addition, embodiments herein contemplate using methods with additional steps, fewer steps, or different steps, so long as the steps remain appropriate for implanting an example stimulation system 10, 100 into a person for electrical stimulation of the person's brain.

Brainstem Stimulation

The stimulation system 10, 100, described above, can be implanted into a person's body with stimulation lead 14 located in communication with a predetermined brainstem tissue and/or area. Such systems that can be used are described in WO2004062470, which is incorporated herein by reference in its entirety.

The predetermined brainstem tissue can be selected from medulla oblongata, pons or mesencephalon, more particular the posterior pons or posterior mesencephalon, Luschka's or Magendie's foramen, and ventrolateral part of the medulla oblongata.

Implantation of a stimulation lead 14 in communication with the predetermined brainstem area can be accomplished via a variety of surgical techniques that are well known to those of skill in the art. For example, an electrical stimulation lead can be implanted on, in, or near the brainstem by accessing the brain tissue through a percutaneous route, an open craniotomy, or a burr hole. Where a burr hole is the means of accessing the brainstem, for example, stereotactic equipment suitable to aid in placement of an electrical stimulation lead 14 on, in, or near the brainstem may be positioned around the head. Another alternative technique can include, a modified midline or retrosigmoid posterior fossa technique.

In certain embodiments, electrical stimulation lead 14 is located at least partially within or below the gray or white matter of the brainstem. Alternatively, a stimulation lead 14 can be placed in communication with the predetermined brainstem area by threading the stimulation lead up the spinal cord column, as described above, which is incorporated herein.

As described above, each of the one or more leads 14 incorporated in stimulation system 10 includes one or more electrodes 18 adapted to be positioned near the target brain tissue and used to deliver electrical stimulation energy to the target brain tissue in response to electrical signals received from IMD 12. A percutaneous lead 14 may include one or more circumferential electrodes 18 spaced apart from one another along the length of lead 14. Circumferential electrodes 18 emit electrical stimulation energy generally radially in all directions and may be inserted percutaneously or through a needle. The electrodes 18 of a percutaneous lead 14 may be arranged in configurations other than circumferentially, for example as in a "coated" lead 14. A laminotomy or paddle style lead 14, such as example leads 14*e-i*, includes one or more directional electrodes 18 spaced apart from one another along one surface of lead 14. Directional electrodes 18 emit electrical stimulation energy in a direction generally perpendicular to the surface of lead 14 on which they are located. Although various types of leads 14 are shown as examples, embodiments herein contemplate stimulation system 10 including any suitable type of lead 14 in any suitable number, including three-dimensional leads and matrix leads as described below. In addition, the leads may be used alone or in combination.

Yet further, a stimulation lead 14 can be Implanted in communication with the predetermined brainstem area by a using stereotactic procedures similar to those described above, which are incorporated herein, for implantation via the cerebrum.

Still further, a predetermined brainstem area can be in directly stimulated by implanting a stimulation lead 14 in communication with a cranial nerve (e.g., olfactory nerve, optic, nerve, oculomotor nerve, trochlear nerve, trigeminal nerve, abducent nerve, facial nerve, vestibulocochlear nerve, glossopharyngeal nerve, vagal nerve, accessory nerve, and the hypoglossal nerve) as well as high cervical nerves (cervical nerves have anastomoses with lower cranial nerves) such that stimulation of a cranial nerve in directly stimulates the predetermined brainstem tissue. Such techniques are further described in U.S. Pat. Nos. 6,721,603; 6,622,047; and 5,335,657, and U.S. Provisional Application 60/591,195 entitled "Stimulation System and Method for Treating a Neurological Disorder" each of which are incorporated herein by reference.

Although example steps are illustrated and described, embodiments herein contemplate two or more steps taking place substantially simultaneously or in a different order. In addition, embodiments herein contemplate using methods with additional steps, fewer steps, or different steps, so long as the steps remain appropriate for implanting stimulation system 10 into a person for electrical stimulation of the predetermined site.

In the auditory system, tonic firing transmits the contents of auditory information, while burst firing transmit the valence or importance attached to that sound (Lisman 1997; Sherman 2001; Swadlow and Gusev 2001). Repetitive stimulus presentation results in decreased neuronal response to that stimulus, known as auditory habituation at the single cell level (Ulanovsky et al., 2003), auditory mismatch negativity at multiple cell level (Naatanen et al., 1993; Ulanovsky et al., 2003).

Tinnitus is a noise in the ears, often described as ringing, buzzing, roaring, or clicking Subjective and objective forms of tinnitus exist, with objective tinnitus often caused by muscle contractions or other internal noise sources in the area proximal to auditory structures. In certain cases, external observers can hear the sound generated by the internal source of objective tinnitus. In subjective forms, tinnitus is audible only to the subject. Tinnitus varies in perceived amplitude, with some subjects reporting barely audible forms and others essentially deaf to external sounds and/or incapacitated by the Intensity of the perceived noise.

Tinnitus is usually constantly present, e.g., a non-rational valence is attached to the internally generated sound, and there is no auditory habituation to this specific sound, at this specific frequency. Thus, tinnitus is the result of hyperactivity of lesion-edge frequencies, and auditory mismatch negativity in tinnitus patients is specific for frequencies located at the audiometrically normal lesion edge (Weisz 2004).

As pathological valence of the tinnitus sound is mediated by burst firing, burst firing is increased in tinnitus in the extralemniscal system (Chen and Jastreboff 1995; Eggermont and Kenmochi 1998; Eggermont 2003), in the inner hair cells (Puel 1995; Puel et al., 2002), the auditory nerve (Moller 1984), the dorsal and external inferior colliculus (Chen and Jastreboff 1995), the thalamus (Jeanmonod, Magnin et al., 1996) and the secondary auditory cortex (Eggermont and Kenmochi 1998; Eggermont 2003). Furthermore, quinine, known to generate tinnitus, induces an increased regularity in burst firing, at the level of the auditory cortex, inferior colliculus and frontal cortex (Gopal and Gross 2004). It is contemplated that tinnitus can only become conscious if an increased tonic firing rate is present in the lemniscal system, generating the sound. This increased firing activity has been demonstrated in the lemniscal dorsal cochlear nucleus (Kaltenbach, Godfrey et al., 1998; Zhang and Kaltenbach 1998; Kaltenbach and Afman 2000; Brozoski, Bauer et al., 2002; Zacharek et al., 2002; Kaltenbach et al., 2004), Inferior colliculus (Jastreboff and Sasaki 1986; Jastreboff, Brennan et al., 1988; Jastreboff 1990) (Gerken 1996) and primary auditory cortex (Komiya, 2000). Interestingly, not only tonic firing is increased generating the tinnitus sound, but also the burst firing (Ochi and Eggermont 1997) (keeping it conscious) at a regular basis. Repetitive burst firing is known to generate tonic gamma band activity (Gray and Singer 1989; Brumberg, 2000). Thus, it is envisioned that embodiments herein can be used to modify burst firing, thus modifying tonic gamma activity.

Burst mode firing boosts the gain of neural signaling of important or novel events by enhancing transmitter release and enhancing dendritic depolarization, thereby increasing synaptic potentiation. Conversely, single spiking mode may be used to dampen neuronal signaling and may be associated with habituation to unimportant events (Cooper 2002). It is believed that the main problem in tinnitus is that the internally generated stimulus does not decay due to the presence of regular bursting activity telling the cortex this signal is important and has to remain conscious.

Thus, in embodiments herein, it is envisioned that the hub stimulation may be applied to stimulate multiple network nodes to treat tinnitus as discussed herein.

In phantom pain the same is noted as in Parkinson's Disease (PD) and tinnitus. In humans, the tonic firing rate increases (Yamashiro et al., 2003), as well as the amount of burst firing in the deafferented receptive fields (Rinaldi et al., 1991; Jeanmonod et al., 1996; Radhakrishnan et al., 1999) in the somatosensory thalamic nuclei (Rinaldi et al., 1991; Lenz et al., 1998), as well as activity in the in the intralaminar nuclei (Weigel and Krauss 2004). Synchrony in firing is also increased. This is similar to what is seen in animal neuropathic pain models (Lombard and Besson 1989; Nakamura and Atsuta 2004) (Yamashiro et al., 1991). These results suggest that in pain decreased spike frequency adaptation and increased excitability develops after injury to sensory neurons. Through decreased $Ca^{2+}$ influx, the cell becomes less stable and more likely to initiate or transmit bursts of action potentials (McCallum et al., 2003).

Thus, it is envisioned that that the neuromodulation system or method of embodiments herein will alter or disrupt neural activity associated with the phantom pain.

In Parkinson's disease (PD), the striatum is viewed as the principal input structure of the basal ganglia, while the internal pallidal segment (GPI) and the substantia nigra pars *reticulata* (SNr) are output structures. Input and output structures are linked via a monosynaptic "direct" pathway and a polysynaptic "indirect" pathway involving the external pallidal segment (GPe) and the subthalamic nucleus (STN). According to current schemes, striatal dopamine (DA) enhances transmission along the direct pathway (via D1 receptors), and reduces transmission over the indirect pathway (via D2 receptors) (Wichmann and DeLong 2003).

Increased firing rates are noted in PD, both in the globus pallidus (Magnin et al., 2000) and the subthalamic nucleus (Levy et al., 2002) and is reversed in successful STN stimulation in PD (Welter et al., 2004; Boraud et al., 1996). Synchronization between firing rates is important: lower frequency oscillations facilitate slow idling rhythms in the motor areas of the cortex, whereas synchronization at high frequency restores dynamic task-related cortical ensemble activity in the gamma band (Brown 2003). In PD, a (hyper) synchronization is related to tremor (Levy et al., 2002), similarly to what is seen in the animal Parkinson model (Raz et al., 2000; Nini et al., 1995).

Two or more firing modes exist in the subthalamic nucleus: tonic firing (68%), phasic or burst firing (25%) and phasic-tonic (7%) (Magarinos-Ascone et al., 2002).

In the monkey MPTP Parkinson model, burst firing, which occurs at 4 to 8 Hz, increases in the STN and Gpi in comparison to normal firing (from 69% and 78% in STN and GPi to 79% and 89%, respectively) (Bergman et al., 1994), as well as burst duration, without increase in the amount of spikes per burst (Bergman et al., 1994). Abnormally increased tonic and phasic activity in STN leads to abnormal GPi activity and is a major factor in the development of parkinsonian motor signs (Wichmann et al., 1994). The percentage of cells with 4- to 8-Hz periodic activity correlates with tremor and is significantly increased from 2% to 16% in STN and from 0.6% to 25% in GPi with the MPTP treatment (Bergman et al., 1994). These cells are also recorded in humans with PD (Hutchison et al., 1997). Furthermore, synchronization increases, e.g., a decrease in independent activity (Raz et al., 2000; Nini et al., 1995), both in tonically firing cells (Raz et al., 2001) and burst firing cells. Thus, it is envisioned that that the neuromodulation or stimulation system or method of embodiments herein will alter or disrupt or override the regular bursting rhythm associated with PD.

Other movement disorders, for example, chorea, Huntington's chorea, hemiballism and parkinsonian tremor all differ in the amount of regularity in their muscle contractions. (Hashimoto and Yanagisawa 1994). The regularities of interval, amplitude, rise time, and EMG activity differs within order of regularity, such PD, vascular chorea, Huntington chorea and hemiballism being least regular (Hashimoto and Yanagisawa 1994). However, in chorea (Hashimoto et al., 2001), hemiballism (Postuma and Lang 2003) and Huntington's disease (Cubo et al., 2000), the firing rate might be decreased in contrast to PD. Burst discharges are, however, correlated to the choreatic movements (Kanazawa et al., 1990), similarly to what is noted in PD (Bergman, Wichmann et al., 1994). Thus, the neuromodulation system and/or method of embodiments herein is used to alter or disrupt neural activity associated with the neurological motor disorder, disease, or condition.

Food presentation in normal healthy, non-obese individuals significantly increases metabolism in the whole brain (24%, P<0.01), and these changes are largest in superior temporal, anterior insula, and orbitofrontal cortices (Wang, Volkow et al., 2004). Food-related visual stimuli elicit greater responses in the amygdala, parahippocampal gyrus and anterior fusiform gyrus when participants are in a hungry state relative to a satiated state (LaBar, Gitelman et al., 2001). Hunger is associated with significantly increased rCBF in the vicinity of the hypothalamus and insular cortex and in addition paralimbic and limbic areas (orbitofrontal cortex, anterior cingulate cortex, and parahippocampal and hippocampal formation), thalamus, caudate, precuneus, putamen, and cerebellum (Tataranni, Gautier et al., 1999). Satiation is associated with increased rCBF in the vicinity of the ventromedial prefrontal cortex, dorsolateral prefrontal cortex, and inferior parietal lobule (Tataranni, Gautier et al., 1999). High-calorie foods yield significant activation within the medial and dorsolateral prefrontal cortex, thalamus, hypothalamus, corpus callosum, and cerebellum. Low-calorie foods yield smaller regions of focal activation within medial orbitofrontal cortex, primary gustatory/somatosensory cortex, and superior, middle, and medial temporal regions (Killgore, Young et al., 2003). Activity within the temporo-insular cortex in normal appetitive function is associated with the desirability or valence of food stimuli, prior to ingestion (Gordon, Dougherty et al., 2000). When a food is eaten to satiety, its reward value decreases. Responses of gustatory neurons in the secondary taste area within the orbitofrontal cortex are modulated by hunger and satiety, in that they stop responding to the taste of a food on which an animal has been fed to behavioral satiation, yet may continue to respond to the taste of other foods (Critchley and Rolls 1996; O'Doherty, Rolls et al., 2000). In the OFC, the rCBF decreases in the medial OFC and increases in the lateral OFC as the reward value of food changes from pleasant to aversive for non-liquid (Small, Zatorre et al., 2001) and liquid foods (Kringelbach, O'Doherty et al., 2003). In the insular gustatory cortex, neuronal responses to gustatory stimuli are not influenced by the normal transition from hunger to satiety. This is in contrast to the responses of a population of neurons recorded in the hypothalamus, which only respond to the taste of food when the monkey is hungry (Yaxley, Rolls et al., 1988).

Brain responses to hunger/satiation in the hypothalamus, limbic/paralimbic areas (commonly associated with the regulation of emotion), and prefrontal cortex (thought to be involved in the inhibition of inappropriate response tendencies) might be different in obese and lean individuals (Del Parigi, Gautier et al., 2002). Compared with lean women, obese women have significantly greater increases in rCBF in the ventral prefrontal cortex and have significantly greater decreases in the paralimbic areas and in areas of the frontal and temporal cortex (Gautier, Del Parigi et al., 2001). In obese women, the rCBF Is higher in the right parietal and temporal cortices during the food exposure than in the control condition. In addition, in obese women the activation of the right parietal cortex is associated with an enhanced feeling of hunger when looking at food (Karhunen, Lappalainen et al., 1997). This significantly higher metabolic activity in the bilateral parietal somatosensory cortex is noted in the regions where sensation to the mouth, lips and tongue are located. The enhanced activity in somatosensory regions involved with sensory processing of food in the obese subjects can make them more sensitive to the rewarding properties of food related to palatability and can be one of the variables contributing to their excess food consumption (Wang, Volkow et al., 2002).

The neuromodulation system and/or method of embodiments herein is used to alter or disrupt the neural activity related to eating disorders in a patient.

Cognitive and psychological disorders In patients suffering from a depression, a hypometabolism and hypoperfusion localized to the left middorsolateral frontal cortex (MDLFC) is noted (Baxter, Schwartz et al., 1989; Brody, Saxena et al., 2001). Furthermore decreased neural activity in the MDLFC, aka the dorsolateral prefrontal cortex, is correlated with severity of depression (Bench, Friston et al., 1992; Bench, Friston et al., 1993; Dolan, Bench et al., 1994) and is reversed upon recovery from depression (Bench, Frackowiak et al., 1995). Electroencephalography demonstrates increased alpha power. Alpha power is thought to be inversely related to neural activity in left frontal regions of the brains of depressed patients (Bruder, Fong et al., 1997).

Metabolic activity in the ventral perigenual ACC is increased in depressed patients relative to control subjects (Videbech, Ravnkilde et al., 2001) and is positively correlated with severity of depression (Drevets 1999). Furthermore, neural activity in this region decreases in response to antidepressant treatment (Brody, Saxena et al., 2001).

The MDLFC occupies the middle frontal and superior frontal gyri and comprises cytoarchitectonic areas 46 and 9/46 (middle frontal gyms) and area 9 (superior frontal gyms) (Paus and Barrett 2004). The MDLFC has connections with sensory areas processing visual (prestriate and inferior temporal cortices), auditory (superior temporal cortex) and somatosensory (parietal cortex) Information (Petrides and Pandya 1999). The MDLFC also reciprocally connects with the anterior and, to a lesser extent, posterior cingulate cortices (Bates and Goldman-Rakic 1993).

Transcranial magnetic stimulation has been performed in the treatment of depression. The left MDLFC is the most common target for rTMS treatment of depression (Paus and Barrett 2004), and rTMS of the left MDLFC modulates the blood-flow response in the ACC (Barrett, Della-Maggiore et al., 2004; Paus and Barrett 2004). High-frequency (20 Hz) and low-frequency (1 Hz) stimulation seem to have an opposite effect. High-frequency stimulation (HFS) increases and low-frequency stimulation (LFS) decreases cerebral blood flow (CBF) and/or glucose metabolism in the frontal cortex and other linked brain regions (Speer, Kimbrell et al., 2000; Kimbrell, Little et al., 1999; and Post, Kimbrell et al., 1999).

Successful treatment of depression with TMS results in normalization of hypoperfusion (with HFS) and normalization hyperperfusion (with LFS) (Kimbrell, Little et al., 1999). Thus, TMS treatment for depression can be proposed using 20 Hz left frontal cortex (Kimbrell, Little et al., 1999; Paus and Barrett 2004) or 1 Hz right frontal cortex (Klein, Kreinin et al., 1999).

In the ACC of the rat, three kinds of burst firing is recorded. Rhythmic burst firing with inter-burst intervals of 80 and 200 ms and non-rhythmic burst firing (Gemmell, Anderson et al., 2002). ACC stimulations evoke both tonic and burst reactions in the dorsolateral prefrontal cortex (Desiraju 1976). Similarly to other cortical areas, the dorsolateral prefrontal cortex has burst firing cells, tonic firing cells and mixed firing cells. Similarly to other areas, the burst firing notices new incoming sensory (auditory, visual) Information, and tonic firing continues as long as the stimulus lasts (Ito 1982). TMS in burst mode is more powerful than TMS in tonic mode. For example, 20 seconds of 5 Hz burst firing with 3 pulses at 50 Hz per burst have the same effect as 10 minutes 1 Hz tonic TMS.

Obsessive-compulsive disorder is a worldwide psychiatric disorder with a lifetime prevalence of 2% and mainly characterized by obsessional ideas and compulsive behaviors and rituals. Bilateral stimulation in the anterior limbs of the internal capsules (Nuttin, Cosyns et al., 1999; Nuttin, Gabriels et al., 2003) or nucleus accumbens stimulation (Sturm, Lenartz et al., 2003) can improve symptoms but at high frequency and high Intensity stimulation.

Tourette syndrome (TS) is a neuropsychiatric disorder with onset in early childhood. It is characterized by tics and often accompanied by disturbances in behavior, such as obsessive-compulsive disorder (OCD). Bilateral thalamic stimulation, with promising results on tics and obsessive-compulsive symptoms has been performed as a treatment. (Visser-Vandewalle, Temel et al., 2003; Temel and Visser-Vandewalle 2004).

The neuromodulation system and/or method of embodiments herein is used to alter or disrupt the neural activity related to mood and/or anxiety disorders in a patient.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. When processor-based, the controller executes program instructions stored in memory to perform the corresponding operations. Additionally or alternatively, the controllers and the controller device may represent circuits that may be implemented as hardware. The above examples are exemplary only, and are thus not intended to limit in any way the definition and/or meaning of the term "controller."

It is to be understood that the subject matter described herein is not limited in its application to the details of construction and the arrangement of components set forth in the description herein or illustrated in the drawings hereof.

The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the Invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 45 U.S.C. §112(f), unless and until such claim limitations expressly use the phrase "means for" followed by a statement of function void of further structure.

What is claimed is:

1. A method to deliver nested stimulation to nerve tissue of interest to treat a neurological disorder, the method comprising:
   setting first parameters that define a carrier waveform, wherein the carrier waveform exhibits a waveform frequency of less than 1 Hz;
   setting second parameters that define a high frequency waveform, wherein at least one of the carrier waveform and high frequency waveform are defined to correspond to physiologic neural oscillations associated with the nerve tissue of interest;
   operating a pulse generator to generate a nested stimulation waveform that combines the carrier waveform and high frequency waveform, the nested stimulation waveform having a plurality of pulse bursts, wherein (1) each of the pulse bursts comprise a plurality of discrete pulses, (2) pulses within each burst are repeated according to a frequency parameter of the high frequency waveform, and (3) an amplitude of each discrete pulse within respective pulse bursts is controlled according to nesting of the high frequency waveform with the carrier waveform such that amplitude peaks of the corresponding plurality of discrete pulses vary within each respective pulse burst; and
   delivering the nested stimulation waveform through one or more electrodes of an implanted stimulation lead to the nerve tissue of interest to treat the neurological disorder.

2. The method of claim 1, wherein the nerve tissue of interest includes brain tissue of interest, and wherein the high frequency waveform corresponding to high-frequency physiologic neural oscillations associated with brain tissue of interest, and wherein the pulse bursts including pulses having a frequency corresponding to the high frequency neural oscillations.

3. The method of claim 1, wherein the carrier waveform exhibits an frequency of 0.01 Hz.

4. The method of claim 3, wherein the pulse bursts are separated from one another with a burst to burst period that corresponds to a frequency of the low-frequency neural oscillations.

5. The method of claim 1, wherein the carrier and high-frequency waveforms are combined through phase to power cross frequency coupling, in which the phase of the carrier waveform modulates the power of the high-frequency waveform.

6. The method of claim 1, wherein the first parameters are set to define the carrier waveform to correspond to a theta wave frequency band, while the second parameters are set to define the high-frequency waveform to correspond to a gamma wave frequency band.

7. The method of claim 1, wherein the nerve tissue of interest includes brain tissue of interest, and further comprising detecting an event of interest through cross-frequency coupling between theta and gamma waves associated with brain tissue of interest and managing the nested stimulation waveform in connection with detection of the event of interest through cross frequency coupling between theta and gamma waves associated with brain tissue of interest.

8. The method of claim 1, wherein the nerve tissue of interest includes brain tissue of interest, and wherein the brain tissue of interest comprises distributed neural modules located in separate regions of the brain, the method further comprising detecting cross frequency coupling between neural oscillations associated with the distributed neural modules that exhibit long-distance communication over neural oscillations within at least one of delta, theta and alpha wave frequency bands and managing the nested stimulation waveform in connection with detection of the cross frequency coupling between neural oscillations associated with the distributed neural modules.

* * * * *